US012805935B2

(12) United States Patent
Cordonnier et al.

(10) Patent No.: US 12,805,935 B2
(45) Date of Patent: Nov. 24, 2026

(54) PATIENT-SPECIFIC SACROILIAC IMPLANT, AND ASSOCIATED SYSTEMS AND METHODS

(71) Applicant: Carlsmed, Inc., Carlsbad, CA (US)

(72) Inventors: Michael J. Cordonnier, Carlsbad, CA (US); Niall Patrick Casey, Carlsbad, CA (US); Shariq Hussain, Vista, CA (US)

(73) Assignee: Carlsmed, Inc., Carlsbad, CA (US)

( * ) Notice: Subject to any disclaimer, the term of this patent is extended or adjusted under 35 U.S.C. 154(b) by 924 days.

(21) Appl. No.: 17/867,621

(22) Filed: Jul. 18, 2022

(65) Prior Publication Data

US 2023/0014384 A1 Jan. 19, 2023

Related U.S. Application Data

(60) Provisional application No. 63/223,405, filed on Jul. 19, 2021.

(51) Int. Cl.
*A61B 34/10* (2016.01)

(52) U.S. Cl.
CPC ........ *A61B 34/10* (2016.02); *A61B 2034/108* (2016.02)

(58) Field of Classification Search
CPC .............. A61B 2034/108; A61B 34/10; A61B 2034/104; A61B 2034/105; G06N 3/09;
(Continued)

(56) References Cited

U.S. PATENT DOCUMENTS 4,704,686 A 11/1987 Aldinger
4,936,862 A 6/1990 Walker et al.
(Continued)

FOREIGN PATENT DOCUMENTS

CN 104318009 A 1/2015
CN 104353121 A 2/2015
(Continued)

OTHER PUBLICATIONS

Yuan et al , "Application of navigation template to fixation of sacral fracture using three-dimensional reconstruction and reverse engineering technique", 2009, pp. 214-217, downloaded from https://mednexus.org/doi/epdf/10.3760/cma.j.issn.1008-1275.2009.04.005 (Year: 2009).*

(Continued)

*Primary Examiner* — Robert E Fennema
*Assistant Examiner* — Olvin Lopez Alvarez
(74) *Attorney, Agent, or Firm* — Ashurst Perkins Coie US LLP

(57) ABSTRACT

Systems and methods for designing and implementing patient-specific surgical procedures and/or medical devices are disclosed. In some embodiments, a method includes receiving a patient data set of a patient. The patient data set is compared to a plurality of reference patient data sets, wherein each of the plurality of reference patient data sets is associated with a corresponding reference patient. A subset of the plurality of reference patient data sets is selected based, at least partly, on similarity to the patient data set and treatment outcome of the corresponding reference patient. Based on the selected subset, at least one surgical procedure or medical device design for treating the patient is generated. In some embodiments, the at least one surgical procedure or medical device design can be used to treat the patient's pelvic region and/or sacroiliac joint.

28 Claims, 11 Drawing Sheets

(58) Field of Classification Search
CPC ...... G06N 20/00; B29C 64/386; B33Y 10/00; B33Y 50/00; B33Y 80/00; G16H 20/40; G16H 30/40; G16H 50/50; G16H 50/70
See application file for complete search history.

(56) References Cited

U.S. PATENT DOCUMENTS

| | | | |
|---|---|---|---|
| 5,431,562 | A | 7/1995 | Andreiko et al. |
| D420,995 | S | 2/2000 | Imamura |
| D436,580 | S | 1/2001 | Navano |
| 6,315,553 | B1 | 11/2001 | Sachdeva |
| 6,540,512 | B1 | 4/2003 | Sachdeva |
| 6,696,073 | B2 | 2/2004 | Boyce et al. |
| 6,772,026 | B2 | 8/2004 | Bradbury |
| 6,932,842 | B1 | 8/2005 | Litschko et al. |
| 6,978,188 | B1 | 12/2005 | Christensen |
| 6,988,241 | B1 | 1/2006 | Guttman |
| 7,174,282 | B2 | 2/2007 | Hollister et al. |
| 7,187,790 | B2 | 3/2007 | Sabol et al. |
| D548,242 | S | 8/2007 | Viegers |
| D614,191 | S | 4/2010 | Takano |
| 7,747,305 | B2 | 6/2010 | Dean et al. |
| 7,756,314 | B2 | 7/2010 | Karau et al. |
| 7,799,077 | B2 | 9/2010 | Lang |
| D633,514 | S | 3/2011 | Tokunaga |
| D656,153 | S | 3/2012 | Imamura |
| 8,246,680 | B2 | 8/2012 | Betz |
| 8,265,949 | B2 | 9/2012 | Haddad |
| 8,275,594 | B2 | 9/2012 | Lin |
| 8,337,507 | B2 | 12/2012 | Lang |
| 8,394,142 | B2 | 3/2013 | Bertagnoli |
| 8,457,930 | B2 | 6/2013 | Shroeder |
| 8,532,806 | B1 | 9/2013 | Masson |
| 8,556,983 | B2 | 10/2013 | Bojarski et al. |
| 8,644,568 | B1 | 2/2014 | Hoffman |
| 8,735,773 | B2 | 5/2014 | Lang |
| 8,758,357 | B2 | 6/2014 | Frey |
| 8,775,133 | B2 | 7/2014 | Schroeder |
| 8,781,557 | B2 | 7/2014 | Dean |
| 8,843,229 | B2 | 9/2014 | Vanasse |
| 8,855,389 | B1 | 10/2014 | Hoffman |
| 8,870,889 | B2 | 10/2014 | Frey |
| 9,020,788 | B2 | 4/2015 | Lang |
| D735,231 | S | 7/2015 | Omiya |
| D737,309 | S | 8/2015 | Kito |
| 9,198,678 | B2 | 12/2015 | Frey et al. |
| 9,208,558 | B2 | 12/2015 | Dean |
| D757,025 | S | 5/2016 | Kim |
| D761,842 | S | 7/2016 | Johnson |
| 9,411,939 | B2 | 8/2016 | Furrer |
| 9,445,907 | B2 | 9/2016 | Meridew |
| 9,452,050 | B2 | 9/2016 | Miles et al. |
| D774,076 | S | 12/2016 | Fuller |
| 9,542,525 | B2 | 1/2017 | Arisoy et al. |
| 9,642,633 | B2 | 5/2017 | Frey et al. |
| 9,693,831 | B2 | 7/2017 | Mosnier et al. |
| 9,707,058 | B2 | 7/2017 | Bassett |
| 9,715,563 | B1 | 7/2017 | Schroeder |
| D797,760 | S | 9/2017 | Tsujimura |
| D797,766 | S | 9/2017 | Ibsies |
| D798,312 | S | 9/2017 | Tsujimura |
| 9,757,245 | B2 | 9/2017 | O'Neil et al. |
| D798,894 | S | 10/2017 | Ibsies |
| 9,775,680 | B2 | 10/2017 | Bojarski et al. |
| 9,782,228 | B2 | 10/2017 | Mosnier et al. |
| D812,628 | S | 3/2018 | Okado |
| 9,993,341 | B2 | 6/2018 | Vanasse |
| 10,034,676 | B2 | 7/2018 | Donner |
| D825,605 | S | 8/2018 | Jann |
| D826,977 | S | 8/2018 | Nakajima |
| 10,089,413 | B2 | 10/2018 | Wirx-Speetjens et al. |
| D841,675 | S | 2/2019 | Hoffman |
| 10,213,311 | B2 | 2/2019 | Mafhouz |
| D845,973 | S | 4/2019 | Jaycobs |
| D845,974 | S | 4/2019 | Cooperman |
| D847,165 | S | 4/2019 | Kolbenheyer |
| D848,468 | S | 5/2019 | Ng |
| D849,029 | S | 5/2019 | Cooperman |
| D849,773 | S | 5/2019 | Jiang |
| 10,292,770 | B2 | 5/2019 | Ryan |
| 10,299,863 | B2 | 5/2019 | Grbic et al. |
| D854,560 | S | 7/2019 | Field |
| D854,561 | S | 7/2019 | Field |
| 10,390,958 | B2 | 8/2019 | Maclennan |
| D860,237 | S | 9/2019 | Li |
| D860,238 | S | 9/2019 | Bhardwaj |
| D866,577 | S | 11/2019 | Eisert |
| D867,379 | S | 11/2019 | Ang |
| D867,389 | S | 11/2019 | Jamison |
| 10,463,433 | B2 | 11/2019 | Turner et al. |
| D870,762 | S | 12/2019 | Mendoza |
| 10,512,546 | B2 | 12/2019 | Kamer et al. |
| 10,517,681 | B2 | 12/2019 | Roh et al. |
| D872,117 | S | 1/2020 | Kobayashi |
| D872,756 | S | 1/2020 | Howell |
| D874,490 | S | 2/2020 | Dodsworth |
| D875,761 | S | 2/2020 | Heffernan |
| D876,454 | S | 2/2020 | Knowles |
| D876,462 | S | 2/2020 | Li |
| D877,167 | S | 3/2020 | Knowles |
| D879,112 | S | 3/2020 | Hejazi |
| 10,588,589 | B2 | 3/2020 | Bregman-Amitai et al. |
| 10,603,055 | B2 | 3/2020 | Donner et al. |
| D880,513 | S | 4/2020 | Wang |
| D881,908 | S | 4/2020 | Sunil |
| D881,910 | S | 4/2020 | Lin |
| 10,621,289 | B2 | 4/2020 | Schroeder |
| 10,631,988 | B2 | 4/2020 | Arnold et al. |
| D884,008 | S | 5/2020 | Thornberg |
| 10,646,236 | B2 | 5/2020 | Donner et al. |
| 10,646,258 | B2 | 5/2020 | Donner et al. |
| 10,736,698 | B2 | 8/2020 | Bohl |
| 10,751,188 | B2 | 8/2020 | Guo et al. |
| D896,825 | S | 9/2020 | Abel |
| D896,828 | S | 9/2020 | Linares |
| D898,054 | S | 10/2020 | Everhart |
| D899,438 | S | 10/2020 | Crafts |
| 10,806,597 | B2 | 10/2020 | Sournac et al. |
| 10,902,944 | B1 | 1/2021 | Casey et al. |
| D916,868 | S | 4/2021 | Evangeliou |
| D916,879 | S | 4/2021 | Mitsumori |
| D918,253 | S | 5/2021 | Choe |
| 11,000,334 | B1 | 5/2021 | Young |
| D921,675 | S | 6/2021 | Kmak |
| D921,677 | S | 6/2021 | Kmak |
| D921,687 | S | 6/2021 | Kmak |
| D924,909 | S | 7/2021 | Nasu |
| D925,567 | S | 7/2021 | Hayamizu |
| D927,528 | S | 8/2021 | Heisler |
| 11,083,586 | B2 | 8/2021 | Cordonnier |
| 11,112,770 | B2 | 9/2021 | Roh et al. |
| D933,692 | S | 10/2021 | Smith |
| 11,166,764 | B2 | 11/2021 | Roh et al. |
| 11,185,369 | B2 | 11/2021 | Ryan |
| D937,870 | S | 12/2021 | Pinto |
| D937,876 | S | 12/2021 | Harvey |
| D938,461 | S | 12/2021 | Hoffman |
| D938,986 | S | 12/2021 | Grossberg |
| D940,178 | S | 1/2022 | Ang |
| D946,022 | S | 3/2022 | Nuttbrown |
| D946,023 | S | 3/2022 | Nuttbrown |
| D946,024 | S | 3/2022 | Vogler-Ivashchanka |
| D946,616 | S | 3/2022 | Tsai |
| D958,151 | S | 7/2022 | Casey et al. |
| 11,376,076 | B2 | 7/2022 | Casey et al. |
| 11,432,943 | B2 | 9/2022 | Casey et al. |
| 11,439,514 | B2 | 9/2022 | Casey et al. |
| 11,540,922 | B2 * | 1/2023 | Arnold .................... A61F 2/446 |
| 2004/0104512 | A1 | 6/2004 | Eidenschink |
| 2007/0276501 | A1 | 11/2007 | Betz |
| 2008/0227047 | A1 | 9/2008 | Lowe |
| 2009/0062739 | A1 | 3/2009 | Anderson |
| 2010/0191071 | A1 * | 7/2010 | Anderson .............. G16H 50/50 703/11 |

(56) References Cited

U.S. PATENT DOCUMENTS

| | | | | |
|---|---|---|---|---|
| 2010/0324692 | A1 | 12/2010 | Uthgenannt | |
| 2011/0184518 | A1* | 7/2011 | Trieu | A61B 17/562 623/17.11 |
| 2012/0150243 | A9 | 6/2012 | Crawford et al. | |
| 2012/0322018 | A1 | 12/2012 | Lowe | |
| 2013/0323669 | A1 | 12/2013 | Lowe | |
| 2014/0072608 | A1 | 3/2014 | Karagkiozaki | |
| 2014/0074438 | A1 | 3/2014 | Furrer | |
| 2014/0081659 | A1 | 3/2014 | Nawana et al. | |
| 2014/0086780 | A1 | 3/2014 | Miller | |
| 2014/0100886 | A1 | 4/2014 | Woods | |
| 2014/0164022 | A1 | 6/2014 | Reed | |
| 2014/0263674 | A1 | 9/2014 | Cerveny | |
| 2014/0350614 | A1 | 11/2014 | Frey | |
| 2015/0079533 | A1 | 3/2015 | Lowe | |
| 2015/0105891 | A1 | 4/2015 | Golway et al. | |
| 2015/0199488 | A1 | 7/2015 | Falchuk | |
| 2015/0213225 | A1 | 7/2015 | Amarasingham | |
| 2015/0324490 | A1 | 11/2015 | Page | |
| 2015/0328004 | A1 | 11/2015 | Mafhouz | |
| 2015/0332018 | A1 | 11/2015 | Rosen | |
| 2016/0001039 | A1 | 1/2016 | Armour et al. | |
| 2016/0015465 | A1 | 1/2016 | Steines et al. | |
| 2016/0030067 | A1 | 2/2016 | Frey et al. | |
| 2016/0074048 | A1 | 3/2016 | Pavlovskaia | |
| 2016/0081810 | A1 | 3/2016 | Riley et al. | |
| 2016/0117817 | A1 | 4/2016 | Seel | |
| 2016/0143744 | A1 | 5/2016 | Bojarski et al. | |
| 2016/0184054 | A1 | 6/2016 | Lowe | |
| 2016/0210374 | A1 | 7/2016 | Mosnier et al. | |
| 2016/0217268 | A1 | 7/2016 | Otto | |
| 2016/0242857 | A1 | 8/2016 | Scholl | |
| 2016/0296159 | A1* | 10/2016 | Larson | G16H 20/00 |
| 2016/0300026 | A1 | 10/2016 | Bogoni et al. | |
| 2016/0354039 | A1 | 12/2016 | Soto et al. | |
| 2016/0378919 | A1 | 12/2016 | McNutt et al. | |
| 2017/0000566 | A1 | 1/2017 | Gordon | |
| 2017/0014169 | A1 | 1/2017 | Dean | |
| 2017/0020679 | A1 | 1/2017 | Maclennan | |
| 2017/0035514 | A1 | 2/2017 | Fox et al. | |
| 2017/0061375 | A1 | 3/2017 | Laster | |
| 2017/0068792 | A1 | 3/2017 | Reiner | |
| 2017/0112548 | A1 | 4/2017 | Alamin et al. | |
| 2017/0135706 | A1 | 5/2017 | Frey et al. | |
| 2017/0143494 | A1 | 5/2017 | Mahfouz | |
| 2017/0143831 | A1 | 5/2017 | Varanasi et al. | |
| 2017/0216047 | A1 | 8/2017 | Hawkes et al. | |
| 2017/0220740 | A1 | 8/2017 | D'Urso | |
| 2017/0252107 | A1 | 9/2017 | Turner et al. | |
| 2017/0262595 | A1 | 9/2017 | Vorhis | |
| 2017/0340447 | A1 | 11/2017 | Mahfouz | |
| 2017/0354510 | A1 | 12/2017 | O'Neil et al. | |
| 2017/0367645 | A1 | 12/2017 | Klinder | |
| 2018/0008349 | A1 | 1/2018 | Gillman | |
| 2018/0104071 | A1* | 4/2018 | Reckling | A61B 17/68 |
| 2018/0113992 | A1 | 4/2018 | Eltorai et al. | |
| 2018/0116727 | A1 | 5/2018 | Caldwell et al. | |
| 2018/0168499 | A1 | 6/2018 | Bergold | |
| 2018/0168731 | A1 | 6/2018 | Reid | |
| 2018/0185075 | A1 | 7/2018 | She | |
| 2018/0233222 | A1 | 8/2018 | Daley | |
| 2018/0233225 | A1 | 8/2018 | Experton | |
| 2018/0250075 | A1 | 9/2018 | Cho | |
| 2018/0296343 | A1* | 10/2018 | Wei | B33Y 50/00 |
| 2018/0303552 | A1 | 10/2018 | Ryan | |
| 2018/0303616 | A1 | 10/2018 | Bhattacharyya et al. | |
| 2018/0308569 | A1 | 10/2018 | Luellen | |
| 2018/0338841 | A1 | 11/2018 | Miller et al. | |
| 2019/0065685 | A1 | 2/2019 | Pickover | |
| 2019/0092669 | A1 | 3/2019 | Arauzo Perez et al. | |
| 2019/0146458 | A1* | 5/2019 | Roh | G05B 19/4099 700/98 |
| 2019/0201106 | A1 | 7/2019 | Siemionow | |
| 2019/0209011 | A1* | 7/2019 | Donner | A61B 5/4528 |
| 2019/0262084 | A1 | 8/2019 | Roh et al. | |
| 2019/0266597 | A1 | 8/2019 | Mohtar | |
| 2019/0290361 | A1* | 9/2019 | Shalayev | A61B 34/10 |
| 2019/0321193 | A1* | 10/2019 | Casey | A61B 17/7007 |
| 2019/0328929 | A1 | 10/2019 | Kugler et al. | |
| 2019/0333622 | A1 | 10/2019 | Levin | |
| 2019/0354693 | A1 | 11/2019 | Yoon | |
| 2019/0380792 | A1 | 12/2019 | Poltaretskyi et al. | |
| 2019/0388131 | A1 | 12/2019 | Mehl et al. | |
| 2020/0021570 | A1 | 1/2020 | Lin | |
| 2020/0078180 | A1 | 3/2020 | Casey et al. | |
| 2020/0085509 | A1 | 3/2020 | Roh et al. | |
| 2020/0170802 | A1 | 6/2020 | Casey et al. | |
| 2020/0261156 | A1 | 8/2020 | Schmidt | |
| 2020/0289288 | A1 | 9/2020 | Müller et al. | |
| 2020/0297495 | A1* | 9/2020 | Gemon | A61F 2/38 |
| 2020/0315708 | A1 | 10/2020 | Mosnier et al. | |
| 2021/0059822 | A1 | 3/2021 | Casey et al. | |
| 2021/0064605 | A1 | 3/2021 | Balint | |
| 2021/0128247 | A1* | 5/2021 | Khan | A61B 34/10 |
| 2021/0145519 | A1 | 5/2021 | Mosnier et al. | |
| 2021/0192759 | A1 | 6/2021 | Lang | |
| 2021/0210189 | A1 | 7/2021 | Casey et al. | |
| 2021/0287770 | A1 | 9/2021 | Anderson | |
| 2021/0382457 | A1 | 12/2021 | Roh et al. | |
| 2022/0000625 | A1 | 1/2022 | Cordonnier | |
| 2022/0006642 | A1 | 1/2022 | Maj et al. | |
| 2022/0039965 | A1 | 2/2022 | Casey et al. | |
| 2022/0047400 | A1* | 2/2022 | Chaoui | G16H 30/20 |
| 2022/0047402 | A1 | 2/2022 | Casey et al. | |
| 2022/0071644 | A1* | 3/2022 | Donner | A61B 17/144 |
| 2022/0110686 | A1 | 4/2022 | Roh et al. | |
| 2022/0160405 | A1 | 5/2022 | Casey et al. | |
| 2022/0160518 | A1 | 5/2022 | Casey et al. | |

FOREIGN PATENT DOCUMENTS

| | | | |
|---|---|---|---|
| CN | 204468348 | U | 7/2015 |
| CN | 105796214 | A | 7/2016 |
| CN | 106202861 | | 12/2016 |
| CN | 107220933 | | 9/2017 |
| CN | 108670506 | A | 10/2018 |
| CN | 110575289 | A | 12/2019 |
| CN | 111281613 | A | 6/2020 |
| CN | 112155792 | A | 1/2021 |
| CN | 113643790 | | 11/2021 |
| EP | 3120796 | A1 | 1/2017 |
| WO | 9507509 | A1 | 3/1995 |
| WO | 2004110309 | A2 | 12/2004 |
| WO | 2010151564 | A1 | 12/2010 |
| WO | 2012154534 | A1 | 11/2012 |
| WO | 2014180972 | A2 | 11/2014 |
| WO | 2016172694 | A1 | 10/2016 |
| WO | 2019112917 | A1 | 6/2019 |
| WO | 2019148154 | A1 | 8/2019 |
| WO | 2022045956 | A1 | 3/2022 |
| WO | 2023003822 | | 3/2023 |

OTHER PUBLICATIONS

Hughes, "Using a Bayesian Network to Predict L5/S1 Spinal Compression Force from Posture, Hand Load, Anthropometry, and Disc Injury Status", pp. 7, 2017, downloaded from https://onlinelibrary.wiley.com/doi/full/10.1155/2017/2014961 (Year: 2017).*

Stuby et al, "Symphyseal fixation in open book injuries cannot fully compensate anterior SI joint injury ĐA biomechanical study in a two-leg alternating load model" pp. 1-11, 2017. downloaded from https://pmc.ncbi.nlm.nih.gov/articles/PMC5703512/ (Year: 2017 ).*

Wagner et al, "Space available for trans-sacral implants to treat fractures of the pelvis assessed by virtual implant positioning", 2019, pp. 1385-1391, downloaded from https://link.springer.com/article/10.1007/s00402-019-03204-9 (Year: 2019).*

Yang et al, "Coronal and sagittal balance in Lenke 5 AIS patients following posterior fusion: important role of the lowest instrument vertebrae selection", pp. 1-10, 2018, downloaded from https://pmc.ncbi.nlm.nih.gov/articles/PMC6038256/pdf/12891_2018_Article_2135.pdf (Year: 2018).*

(56) References Cited

OTHER PUBLICATIONS

ISA: United States Patent and Trademark Office, PCT Application No. PCT/US22/37500, filed Jul. 18, 2022, International Search Report and Written Opinion mailed Dec. 28, 2022, 19 pages.
Endo, Kenji et al. "Measurement of whole spine sagittal alignment using the SLOT radiography of the SonialVision safire series clinical application." Medical Now, No. 78; Aug. 2015, 4 pages.
Eshkalak, S.K. et al., "The role of three-dimensional printing in healthcare and medicine." Materials and Design 194, Jul. 10, 20202, 15 pages.
Extended European Search Report for European Application No. 18885367.5, mailed Aug. 16, 2021, 8 pages.
Extended European Search Report for European Application No. 19859930.0, mailed Jun. 22, 2022, 7 pages.
International Search Report and Written Opinion for International Application No. PCT/US19/50885, mailed Jan. 28, 2020, 21 pages.
International Search Report and Written Opinion for International Application No. PCT/US19/63855, mailed Feb. 14, 2020, 15 pages.
International Search Report and Written Opinion for International Application No. PCT/US21/44878, mailed Nov. 16, 2021, 18 pages.
International Search Report and Written Opinion for International Application No. PCT/US21/45503, mailed Jan. 11, 2022, 19 pages.
International Search Report and Written Opinion for International Patent Application No. PCT/US21/60074, mailed Mar. 17, 2022, 21 pages.
International Search Report and Written Opinion for International Patent Application No. PCT/US2018/063530, mailed Feb. 12, 2019, 16 pages.
International Search Report and Written Opinion for International Patent Application No. PCT/US21/12065, mailed Apr. 29, 2021, 19 pages.
International Search Report and Written Opinion for International Patent Application No. PCT/US21/59837, mailed Feb. 7, 2022, 19 pages.
Majdouline et al., "Preoperative assessment and evaluation of instrumentation strategies for the treatment of adolescent idiopathic scoliosis: computer simulation and optimization." Scoliosis 7, 21 (2012), pp. 1-8.
Materialise Mimics, "Efficiently turn scans into accurate virtual 3D models," Retrieved on Nov. 1, 2019 at www. materialize.com/en/medical/software/mimics, 1 page.
Pimenta, Dr. Luiz, "Current Surgical Strategies to Restore Proper Sagittal Alignment," Journal of Spine 2015, vol. 4, Issue 4, 2 pages.
Pruthi, G. et al., "Comprehensive review of guidelines to practice prosthodontic and implant procedures during COVID-19 pandemic." Journal of Oral Biology and Craniofacial Research 10, Oct. 17, 2020, 8 pages.
Extended European Search Report for European Application No. 22846472.3; Date of Mailing: Apr. 25, 2025; 10 pages.

* cited by examiner

PATIENT-SPECIFIC SACROILIAC IMPLANT, AND ASSOCIATED SYSTEMS AND METHODS

CROSS-REFERENCE TO RELATED APPLICATION

This application claims priority to U.S. Prov. App. No. 63/223,405, filed Jul. 19, 2021, the entirety of which is hereby incorporated by reference herein.

TECHNICAL FIELD

The present disclosure is generally related to designing and implementing medical care, and more particularly to systems and methods for designing and implementing surgical procedures and/or medical devices.

BACKGROUND

Numerous types of data associated with patient treatments and surgical interventions are available. To determine treatment protocols for a patient, physicians often rely on a subset of patient data available via the patient's medical record and historical outcome data. However, the amount of patient data and historical data may be limited, and the available data may not be correlated or relevant to the particular patient to be treated. Additionally, although digital data collection and processing power have improved, technologies using collected data to determine optimal treatment protocols have lagged. For example, conventional technologies in the field of orthopedics may lack the capability to draw upon large data sets to generate and optimize patient-specific treatments (e.g., surgical interventions and/or implant designs) to achieve favorable treatment outcomes.

BRIEF DESCRIPTION OF THE DRAWINGS

The accompanying drawings illustrate various embodiments of systems, methods, and embodiments of various other aspects of the disclosure. Any person with ordinary skill in the art will appreciate that the illustrated element boundaries (e.g., boxes, groups of boxes, or other shapes) in the figures represent one example of the boundaries. It may be that in some examples one element may be designed as multiple elements or that multiple elements may be designed as one element. In some examples, an element shown as an internal component of one element may be implemented as an external component in another, and vice versa. Furthermore, elements may not be drawn to scale. Non-limiting and non-exhaustive descriptions are described with reference to the following drawings. The components in the figures are not necessarily to scale, emphasis instead being placed upon illustrating principles.

DETAILED DESCRIPTION

Figure 1A:
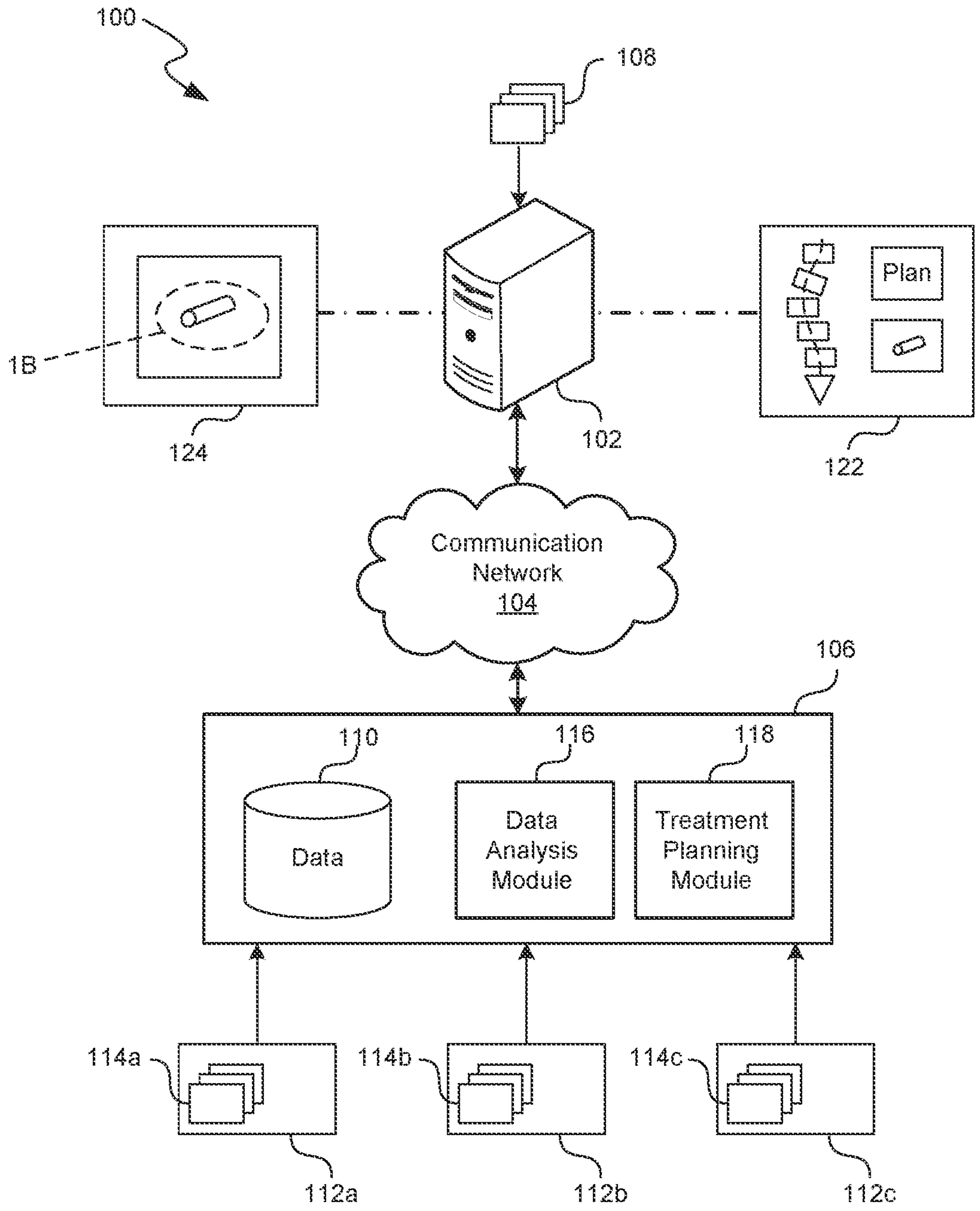
FIG. 1A is a network connection diagram illustrating a system for providing patient-specific medical care, configured in accordance with embodiments of the present technology.

The present technology is directed to systems and methods for planning and implementing medical procedures and/or devices. For example, in many of the embodiments disclosed herein, a method of providing medical care includes comparing a patient data set of a patient to be treated with a plurality of reference patient data sets (e.g., data from previously-treated patients). The method can include selecting a subset of the reference patient data sets, e.g., based on a similarity of the reference patient data set to the patient data set and/or whether the reference patient had a favorable treatment outcome. The selected subset of the reference patient data sets can be used to generate a surgical procedure and/or medical device design that is likely to produce a favorable treatment outcome for the particular patient. In some embodiments, the selected subset is analyzed to identify correlations between patient pathology, surgical procedures, device designs, and/or treatment outcomes, and these correlations are used to determine a personalized treatment protocol with a higher likelihood of success.

In some embodiments the method can include using the patient data and/or the reference patient data sets to generate a surgical procedure and/or medical device design for treating a patient's pelvic region, such as a patient's sacrum, ilium, and/or sacroiliac joint. The medical device design can include one or more implants and/or insertion or delivery instruments. The surgical procedure can include one or more locations and/or trajectories (e.g., insertion trajectories or angles) for implanting the medical device design or implant(s). The medical device design and/or surgical procedure can correspond to the patient data, such that one or more aspects or elements of the medical device design and/or surgical procedure can correspond to the patient's specific anatomy. For example, an implant designed for use in a procedure to fuse (e.g., couple, fix, join, etc.) a patient's sacroiliac joint can have dimension(s), shape(s), contour(s), and/or curvature that corresponds to the dimension(s), shape(s), contour(s), and/or curvature of the patient's sacrum, ilium, and/or sacroiliac joint. The patient data and/or reference patient data sets can include images, biomechanical data (e.g., range of motion, posture data, compressive forces, shear forces, tensile forces, etc.), pain data, physician notes, or the like. Pain data can include pain scores, such as lower back, hip, and/or leg pain scores based on questionnaires or tests, such as patient feedback (e.g., pain score) during pelvic gapping, pelvic compression, thigh thrusting, flexion abduction external rotation (FABER) test, and/or Gaenslen test. In some embodiments, the pain data can include pain reduction data, such as a change in the pain scores before and after surgical intervention. Accordingly, in some embodiments the method can include generating a surgical procedure and/or medical device design associated with relatively low pain scores and/or relatively high pain reduction scores.

In the context of surgery, systems with improved computing capabilities (e.g., predictive analytics, machine learning, neural networks, artificial intelligence (AI)) can use large data sets to define improved or optimal surgical interventions and/or implant designs for a specific patient. The patient's entire data can be characterized and compared to aggregated data from groups of prior patients (e.g., parameters, metrics, pathologies, treatments, outcomes). In some embodiments, the systems described herein use this aggregated data to formulate potential treatment solutions (e.g., surgical plans and/or implant designs for spine and orthopedic procedures) and analyze the associated likelihood of success. These systems can further compare potential treatment solutions to determine an optimal patient-specific solution that is expected to maximize the likelihood for a successful outcome.

For example, if a patient presents with a spinal deformity pathology that can be described with data including lumbar lordosis, Cobb angles, pain data, coronal parameters (e.g., coronal balance, global coronal balance, coronal pelvic tilt, etc.), sagittal parameters (e.g., pelvic incidence, sacral slope, thoracic kyphosis, etc.) and/or pelvic parameters, an algorithm using these data points as inputs can be used to describe an optimal surgical plan and/or implant design to correct the subject pathology and improve the patient's outcome. As additional data inputs are used to describe the pathology (e.g., disc height, segment flexibility, bone quality, rotational displacement), the algorithm can use these additional inputs to further define an optimal surgical plan and/or implant design for that particular patient and their pathology. In some embodiments the additional data inputs can include one or more measurements corresponding to a patient's sacrum, ilium, and/or sacroiliac joint, such as one or more dimensions (e.g., height, width, length, thickness, position, relative position, etc.) and/or properties (e.g., density, curvature, tensile strength, flexibility, range of motion, etc.) thereof. The one or more measurements can include: sacral width, sacral pelvic surface curvature, sacral dorsal surface curvature, sacral lateral surface curvature, sacroiliac joint width, sacroiliac joint length, sacroiliac joint range of movement, sacroiliac joint curvature, sacroiliac joint position, sacroiliac joint topology, bone surface curvature(s), and/or any other measurement or data input described herein. These measurements can be used, for example, to define an optimal surgical plan and/or implant design to treat a particular patient's sacroiliac joint.

In some embodiments, the present technology can automatically or at least semi-automatically determine a corrected anatomical configuration for a subject patient suffering from one or more deformities. For example, the computing systems described herein can apply mathematical rules for select parameters (e.g., lumbar lordosis, Cobb angles, pain data, pelvic parameters, etc.) and/or identify similar patients by analyzing reference patient data sets, and, based on the rules and/or comparison to other patients, can provide a recommended anatomical configuration that represents the optimal outcome if the subject patient were to undergo surgery. In some embodiments, the systems and methods described herein generate a virtual model of the corrected/recommended anatomical configuration (e.g., for surgeon review).

In some embodiments, the present technology can also automatically or at least semi-automatically generate a surgical plan for achieving a previously-identified corrected anatomical configuration for a subject patient. For example, based off the virtual model of the corrected anatomical configuration, the systems and methods herein can determine a type of surgery (e.g., spinal fusion surgery, non-fusion surgery, pelvic surgery, etc.), a surgical approach (e.g., anterior, posterior, etc.), and/or spinal parameters for the corrected anatomical configuration (e.g., lumbar lordosis, Cobb angle, pain score(s), pelvic parameters, etc.). The surgical plan can be transmitted to a surgeon for review and approval. In some embodiments, the present technology can also design one or more patient-specific implants for achieving the corrected anatomical configuration via the surgical plan.

In some embodiments, the present technology provides systems and methods that generate multiple anatomical models of the patient. For example, a first model may show the patient's native (e.g., pre-operative) anatomical configuration, and a second model may provide a simulation of the patient's corrected (e.g., post-operative) anatomical configuration. The second virtual model may optionally include one or more virtual implants shown as implanted at one or more target regions of the patient. Spine metrics (e.g., lumbar lordosis, Cobb angles, coronal parameters, sagittal parameters, pelvic parameters, pain data, etc.) can also be provided for both the pre-operative anatomical configuration and expected post-operative anatomical configuration.

In some embodiments, the present technology includes generating, designing, and/or providing patient-specific medical procedures for multiple locations within a patient. For example, the present technology can include identifying at least two target regions or sites within a patient (e.g., a first vertebral level and a second vertebral level; a sacral-iliac, sacroiliac, or "SI" joint; and the like) for surgical intervention. The present technology can then design at least two patient-specific implants for implantation at the at least two target regions. The at least two patient-specific implants can each be specifically designed for their respective target region, and thus can have different geometries. In some embodiments, the corrected anatomical configuration of the patient is only achieved by implanting each of the at least two patient-specific implants. In the context of spinal surgery, for example, the present technology may provide a first patient-specific interbody device to be implanted between the L2 and L3 vertebrae, a second patient-specific interbody device to be implanted between the L3 and L4 vertebrae, and a third patient-specific interbody device to be implanted between the L4 and L5 vertebrae. In the context of sacroiliac fusion, for example, the present technology may provide a first patient-specific fusion device to be implanted between the sacrum and right ilium, and a second patient-specific fusion device to be implanted between the sacrum and the left ilium. Additionally, each of the patient-specific interbody devices and/or patient-specific fusion devices can be designed to be inserted via a specific path or process and/or at a specific trajectory or angle. The implant can be configured to conform to the interior of the joint or exterior of the ilium.

In some embodiments, the present technology can predict, model, or simulate disease progression within a particular patient to aid in diagnosis and/or treatment planning. The simulation can be done to model and/or estimate future anatomical configurations and/or spine metrics of the patient (a) if no surgical intervention occurs, or (b) for a variety of different surgical intervention options. The progression modeling can thus be used to determine the optimal time for surgical intervention and/or to select which surgical intervention provides the best long-term outcomes. In some embodiments, the disease progression modelling is performed using one or more machine learning models trained based on a plurality of reference patients.

In some embodiments, the present technology can include biomechanical models or simulations. In at least some embodiments, for example, the biomechanical simulation(s) can model, simulate, or otherwise predict the effect of one or more forces or loads on a particular patient's anatomy, e.g., to model and/or estimate future anatomical configurations and/or spine metrics of the patient (a) if no surgical intervention occurs, and/or (b) for a variety of different surgical intervention options. The biomechanical simulation(s) can be used to simulate loading based on a range of motion of a patient's spine or SI joint before and/or after surgical intervention. In at least some embodiments, for example, the present technology can include performing a biomechanical simulation of spinal load transfer via the sacroiliac joint(s) to one or more of the patient's coxal bones (e.g., the ilium) over a range of motion of the patient's spine. The simulated loading can be used to predict one or more post-operative forces or loads on the patient's anatomy. In at least some embodiments, for example, the simulated loading can be used to predict a post-operative compressive force and/or a post-operative shear force on at least one of a patient's sacroiliac joints. In some embodiments, the biomechanical simulations can include modeling one or more muscles and/or ligaments operably coupled to at least a portion of a patient's anatomy (e.g., a spine, one or more vertebral bodies, a femur, the sacrum, the ilium, etc.), and predicting one or more forces applied to at least one of a patient's sacroiliac joints based on the modeled muscle(s) and/or ligament(s). In some embodiments, the biomechanical simulations can be used to determine an acceptable loading on the sacroiliac joint(s) and/or one or more vertebral bodies. Thus, in some embodiment the biomechanical simulation(s) can be used to determine whether the simulated loading before and/or after surgical intervention is acceptable, e.g., by comparing the simulated loading and the acceptable loading. In some embodiments, the simulating loading and/or the acceptable loading can be used to generate, design, and/or provide one or more patient-specific medical procedures and/or devices. In some embodiments, the biomechanical simulations can be performed using one or more virtual three-dimensional models of the patient's anatomy in a native configuration and/or in a corrected configuration.

In a particular non-limiting example, the present technology includes a method for providing patient-specific medical care for a subject patient. The method can include receiving a patient-data set for the subject patient that includes one or more images of the patient's spinal region showing the patient's native anatomical configuration. The method can further include determining a corrected anatomical configuration for the subject patient that is different than the native anatomical configuration, and creating a virtual model of the corrected anatomical configuration. The method can further include generating surgical plan and designing one or more patient-specific implants for achieving the corrected anatomical configuration in the subject patient. In representative embodiments, the foregoing method can be performed by a system storing computer-executable instructions that, when executed, cause the system to perform the steps of method.

In a particular non-limiting example, the present technology includes a method for designing a patient-specific sacroiliac joint implant ("the implant") for a subject patient. The method can include receiving a patient data set of the subject patient, the patient data set including spinal pathology data for the subject patient. The patient data set can be compared to a plurality of reference patient data sets to identify one or more similar patient data sets in the plurality of reference patient data sets, with each identified similar patient data set corresponding to a reference patient having similar spinal pathology to the subject patient and who received treatment with a sacroiliac joint implant. The method can further include selecting a subset of the one or more similar patient data sets based on whether the similar patient data sets indicated the reference patient had a favorable outcome following implantation of their implant. The method can further include identifying, for at least one similar reference patients of the selected subset, surgical procedure data and design data for the respective implant that produced the favorable outcome in the similar reference patient. Based on the design data and the surgical produced data that produced the favorable outcome in the similar reference patient, the patient-specific implant for the subject patient and a surgical procedure for implanting the patient-specific implant into the subject patient can be designed. In some embodiments, the method can further include outputting fabrication instructions for causing a manufacturing system to manufacture the patient-specific sacroiliac joint implant according to the generated design. In representative embodiments, the foregoing method can be performed by a system storing computer-executable instructions that, when executed, cause the system to perform the steps of method.

In some embodiments, the patient-specific implant can be used to fuse a sacroiliac joint in the subject patient. The patient-specific implant can be or include one or more patient-specific intrajoint implants (e.g., positioned generally or substantially within the sacroiliac joint and/or between the sacrum and ilium,) and/or one or more patient-specific transverse joint implants (e.g., positioned generally or substantially across or through the sacroiliac joint). Examples of types of such patient-specific implants include, but are not limited to, screws (e.g., bone screws, spinal screws, pedicle screws, facet screws), interbody implant devices (e.g., intervertebral implants), cages, plates, rods, disks, fusion devices, spacers, rods, expandable devices, stents, brackets, ties, scaffolds, fixation device, anchors, nuts, bolts, rivets, connectors, tethers, fasteners, joint replacements (e.g., artificial discs), hip implants, or the like. In some embodiments, two or more of the same or different types of implants (e.g., two or more of the same type of implant and/or individual ones of at least two different types of implants) can be combined, used in conjunction, and/or operably associated to form the patient-specific implant. The patient-specific implant can include one or more patient-specific elements or features, and the design for and/or method of using the patient-specific implant can be based on the patient data set of the subject patient. For example, in at least some embodiments the patient-specific implant and/or one or more elements or features thereof can be designed to be inserted (e.g., placed, positioned, implanted, etc.) at a specific location (e.g., a sacral vertebra, a vertebral level, an angle of insertion, etc.), designed to have one or more characteristics (e.g., length, width, diameter, cross-sectional shape, curvature, density, porosity, material property(ies), etc.) based on the patient's anatomy, and/or designed to correspond with one or more patient-specific sacroiliac anatomical features (e.g., lateral contour(s), sacroiliac joint shape(s), topology(ies), etc.) based on the patient data set. In at least some embodiments the patient-specific implant can include a contact or support surface positionable to at least partially contact the patient's sacroiliac joint, and the contact or support surface can be designed to have a shape or curvature that matches and/or corresponds to the shape or curvature of the patient's sacroiliac joint.

In some embodiments, the present technology includes a method for providing patient-specific medical care for a patient's sacroiliac joint. The method can include receiving a patient-data set for the patient that includes one or more images of the patient's sacroiliac joint showing the patient's native anatomical configuration. In some embodiments, the one or more images can additionally include at least a portion of the patient's spine/spinal anatomy. The method can further include determining a corrected anatomical configuration for the patient's sacroiliac joint and/or spine that is different than the native anatomical configuration, and creating a virtual model of the patient's sacroiliac joint and/or spine in corrected anatomical configuration. The method can further include generating a surgical plan and designing one or more patient-specific sacroiliac joint implants for achieving the corrected anatomical configuration in the patient. In representative embodiments, the foregoing method can be performed by a system storing computer-executable instructions that, when executed, cause the system to perform the steps of method.

In some embodiments, the present technology includes a method for designing one or more patient-specific instruments or delivery devices ("the instrument" or "the instruments"). The instruments can be designed based on the patient data set and/or a design for a patient-specific implant, such as a patient-specific sacroiliac implant. The instruments can include one or more cannulas, rods, shafts, delivery devices, connectors, etc. The instruments can be used during one or more steps of a surgical plan, such as a patient-specific surgical plan designed based on patient data sets, as described previously. For example, the instruments can be used to incise or cut tissue (e.g., bone, skin, muscle, etc.), remove tissue (e.g., drill, prepare a trans-articular sacroiliac joint space, etc.), insert or deliver one or more implants (e.g., one or more patient-specific implants), and/or insert or deliver one or more elements of an implant (e.g., to couple or connect one or more screws, pins, rods, anchors, etc. to an implant body).

Embodiments of the present disclosure will be described more fully hereinafter with reference to the accompanying drawings in which like numerals represent like elements throughout the several figures, and in which example embodiments are shown. Embodiments of the claims may, however, be embodied in many different forms and should not be construed as limited to the embodiments set forth herein. The examples set forth herein are non-limiting examples and are merely examples among other possible examples.

The words "comprising," "having," "containing," and "including," and other forms thereof, are intended to be equivalent in meaning and be open ended in that an item or items following any one of these words is not meant to be an exhaustive listing of such item or items, or meant to be limited to only the listed item or items.

As used herein and in the appended claims, the singular forms "a," "an," and "the" include plural references unless the context clearly dictates otherwise.

Although the disclosure herein primarily describes systems and methods for treatment planning in the context of orthopedic surgery, the technology may be applied equally to medical treatment and devices in other fields (e.g., other types of surgical practice). Additionally, although many embodiments herein describe systems and methods with respect to implanted devices, the technology may be applied equally to other types of medical devices (e.g., non-implanted devices).

FIG. 1A is a network connection diagram illustrating a computing system 100 for providing patient-specific medical care, configured in accordance with embodiments of the present technology. As described in further detail herein, the system 100 is configured to generate a medical treatment plan for a patient. In some embodiments, the system 100 is configured to generate a medical treatment plan for a patient suffering from an orthopedic or spinal disease or disorder, such as trauma (e.g., fractures), cancer, deformity, degeneration, pain (e.g., back pain, leg pain, sacroiliac joint pain, pain involving sacroiliac joint dysfunction, etc.), irregular spinal curvature (e.g., scoliosis, lordosis, kyphosis), irregular spinal displacement (e.g., spondylolisthesis, lateral displacement axial displacement), osteoarthritis, lumbar degenerative disc disease, cervical degenerative disc disease, lumbar spinal stenosis, or cervical spinal stenosis, or a combination thereof. The medical treatment plan can include surgical information, surgical plans, technology recommendations (e.g., device and/or instrument recommendations), and/or medical device designs. For example, the medical treatment plan can include at least one treatment procedure (e.g., a surgical procedure or intervention) and/or at least one medical device (e.g., an implanted medical device (also referred to herein as an "implant" or "implanted device") or implant delivery instrument).

In some embodiments, the system 100 generates a medical treatment plan that is customized for a particular patient or group of patients, also referred to herein as a "patient-specific" or "personalized" treatment plan. The patient-specific treatment plan can include at least one patient-specific surgical procedure and/or at least one patient-specific medical device that are designed and/or optimized for the patient's particular characteristics (e.g., condition, anatomy, pathology, condition, medical history). For example, the patient-specific medical device can be designed and manufactured specifically for the particular patient, rather than being an off-the-shelf device. However, it shall be appreciated that a patient-specific treatment plan can also include aspects that are not customized for the particular patient. For example, a patient-specific or personalized surgical procedure can include one or more instructions, portions, steps, etc. that are non-patient-specific. Likewise, a patient-specific or personalized medical device can include one or more components that are non-patient-specific, and/or can be used with an instrument or tool that is non-patient-specific. Personalized implant designs can be used to manufacture or select patient-specific technologies, including medical devices, instruments, and/or surgical kits. For example, a personalized surgical kit can include one or more patient-specific devices, patient-specific instruments, non-patient-specific technology (e.g., standard instruments, devices, etc.), instructions for use, patient-specific treatment plan information, or a combination thereof.

The system 100 includes a client computing device 102, which can be a user device, such as a smart phone, mobile device, laptop, desktop, personal computer, tablet, phablet, or other such devices known in the art. As discussed further herein, the client computing device 102 can include one or more processors, and memory storing instructions executable by the one or more processors to perform the methods described herein. The client computing device 102 can be associated with a healthcare provider that is treating the patient. Although FIG. 1A illustrates a single client computing device 102, in alternative embodiments, the client computing device 102 can instead be implemented as a client computing system encompassing a plurality of computing devices, such that the operations described herein with respect to the client computing device 102 can instead be performed by the computing system and/or the plurality of computing devices.

The client computing device 102 is configured to receive a patient data set 108 associated with a patient to be treated. The patient data set 108 can include data representative of the patient's condition, anatomy, pathology, medical history, preferences, and/or any other information or parameters relevant to the patient. For example, the patient data set 108 can include medical history, surgical intervention data, treatment outcome data, progress data (e.g., physician notes), patient feedback (e.g., feedback acquired using quality of life questionnaires, surveys), clinical data, provider information (e.g., physician, hospital, surgical team), patient information (e.g., demographics, sex, age, height, weight, type of pathology, occupation, activity level, tissue information, health rating, comorbidities, health related quality of life (HRQL)), vital signs, diagnostic results, medication information, allergies, image data (e.g., camera images, Magnetic Resonance Imaging (MRI) images, ultrasound images, Computerized Aided Tomography (CAT) scan images, Positron Emission Tomography (PET) images, X-Ray images), diagnostic equipment information (e.g., manufacturer, model number, specifications, user-selected settings/configurations, etc.), or the like. In some embodiments, the patient data set 108 includes data representing one or more of patient identification number (ID), age, gender, body mass index (BMI), lumbar lordosis, Cobb angle(s), pelvic incidence, disc height, segment flexibility, bone quality, rotational displacement, sacroiliac joint anatomy (e.g., dimension(s), property(s), curvature, shape, etc.), and/or treatment level of the spine.

The client computing device 102 is operably connected via a communication network 104 to a server 106, thus allowing for data transfer between the client computing device 102 and the server 106. The communication network 104 may be a wired and/or a wireless network. The communication network 104, if wireless, may be implemented using communication techniques such as Visible Light Communication (VLC), Worldwide Interoperability for Microwave Access (WiMAX), Long term evolution (LTE), Wireless local area network (WLAN), Infrared (IR) communication, Public Switched Telephone Network (PSTN), Radio waves, and/or other communication techniques known in the art.

The server 106, which may also be referred to as a "treatment assistance network" or "prescriptive analytics network," can include one or more computing devices and/or systems. As discussed further herein, the server 106 can include one or more processors, and memory storing instructions executable by the one or more processors to perform the methods described herein. In some embodiments, the server 106 is implemented as a distributed "cloud" computing system or facility across any suitable combination of hardware and/or virtual computing resources.

The client computing device 102 and server 106 can individually or collectively perform the various methods described herein for providing patient-specific medical care. For example, some or all of the steps of the methods described herein can be performed by the client computing device 102 alone, the server 106 alone, or a combination of the client computing device 102 and the server 106. Thus, although certain operations are described herein with respect to the server 106, it shall be appreciated that these operations can also be performed by the client computing device 102, and vice-versa.

The server 106 includes at least one database 110 configured to store reference data useful for the treatment planning methods described herein. The reference data can include historical and/or clinical data from the same or other patients, data collected from prior surgeries and/or other treatments of patients by the same or other healthcare providers, data relating to medical device designs, data collected from study groups or research groups, data from practice databases, data from academic institutions, data from implant manufacturers or other medical device manufacturers, data from imaging studies, data from simulations, clinical trials, demographic data, treatment data, outcome data, mortality rates, or the like.

In some embodiments, the database 110 includes a plurality of reference patient data sets, each patient reference data set associated with a corresponding reference patient. For example, the reference patient can be a patient that previously received treatment or is currently receiving treatment. Each reference patient data set can include data representative of the corresponding reference patient's condition, anatomy, pathology, medical history, disease progression, preferences, and/or any other information or parameters relevant to the reference patient, such as any of the data described herein with respect to the patient data set 108. In some embodiments, the reference patient data set includes pre-operative data, intra-operative data, and/or post-operative data. For example, a reference patient data set can include data representing one or more of patient ID, age, gender, BMI, lumbar lordosis, Cobb angle(s), pelvic incidence, disc height, segment flexibility, bone quality, rotational displacement, sacroiliac joint anatomy (e.g., dimension(s), property(s), surface topology, curvature, shape, etc.), and/or treatment level of the spine. Additionally, or alternatively, the reference patient data set can include treatment data regarding at least one treatment procedure performed on the reference patient, such as descriptions of surgical procedures or interventions (e.g., surgical approaches, bony resections, surgical maneuvers, corrective maneuvers, placement of implants or other devices). In some embodiments, the treatment data includes medical device design data for at least one medical device used to treat the reference patient, such as physical properties (e.g., size, shape, volume, material, mass, weight), mechanical properties (e.g., stiffness, strength, modulus, hardness), and/or biological properties (e.g., osteo-integration, cellular adhesion, anti-bacterial properties, anti-viral properties). In these and other embodiments, the reference patient data set can include outcome data representing an outcome of the treatment of the reference patient, such as corrected anatomical metrics, presence of fusion, HRQL, activity level, return to work, complications, recovery times, efficacy, mortality, and/or follow-up surgeries.

In some embodiments, the server 106 receives at least some of the reference patient data sets from a plurality of healthcare provider computing systems (e.g., systems 112*a*-112*c*, collectively 112). The server 106 can be connected to the healthcare provider computing systems 112 via one or more communication networks (not shown). Each healthcare provider computing system 112 can be associated with a corresponding healthcare provider (e.g., physician, surgeon, medical clinic, hospital, healthcare network, etc.). Each healthcare provider computing system 112 can include at least one reference patient data set (e.g., reference patient data sets 114*a*-114*c*, collectively 114) associated with reference patients treated by the corresponding healthcare provider. The reference patient data sets 114 can include, for example, electronic medical records, electronic health records, biomedical data sets, etc. The reference patient data sets 114 can be received by the server 106 from the healthcare provider computing systems 112 and can be reformatted into different formats for storage in the database 110. Optionally, the reference patient data sets 114 can be processed (e.g., cleaned) to ensure that the represented patient parameters are likely to be useful in the treatment planning methods described herein.

As described in further detail herein, the server 106 can be configured with one or more algorithms that generate patient-specific treatment plan data (e.g., treatment procedures, medical devices) based on the reference data. In some embodiments, the patient-specific data is generated based on correlations between the patient data set 108 and the reference data. Optionally, the server 106 can predict outcomes, including recovery times, efficacy based on clinical end points, likelihood of success, predicted mortality, predicted related follow-up surgeries, or the like. In some embodiments, the server 106 can continuously or periodically analyze patient data (including patient data obtained during the patient stay) to determine near real-time or real-time risk scores, mortality prediction, etc.

In some embodiments, the server 106 includes one or more modules for performing one or more steps of the patient-specific treatment planning methods described herein. For example, in the illustrated embodiment, the server 106 includes a data analysis module 116 and a treatment planning module 118. In other embodiments, one or more of these modules may be combined with each other, or may be omitted. Thus, although certain operations are described herein with respect to a particular module or modules, this is not intended to be limiting, and such operations can be performed by a different module or modules in alternative embodiments.

The data analysis module 116 is configured with one or more algorithms for identifying a subset of reference data from the database 110 that is likely to be useful in developing a patient-specific treatment plan. For example, the data analysis module 116 can compare patient-specific data (e.g., the patient data set 108 received from the client computing device 102) to the reference data from the database 110 (e.g., the reference patient data sets) to identify similar data (e.g., one or more similar patient data sets in the reference patient data sets). The comparison can be based on one or more parameters, such as age, gender, BMI, lumbar lordosis, pelvic incidence, sacroiliac joint anatomy (e.g., dimension(s), property(s), curvature, topology, shape, etc.), and/or treatment levels. The parameter(s) can be used to calculate a similarity score for each reference patient. The similarity score can represent a statistical correlation between the patient data set 108 and the reference patient data set. Accordingly, similar patients can be identified based on whether the similarity score is above, below, or at a specified threshold value. For example, as described in greater detail below, the comparison can be performed by assigning values to each parameter and determining the aggregate difference between the subject patient and each reference patient. Reference patients whose aggregate difference is below a threshold can be considered to be similar patients.

The data analysis module 116 can further be configured with one or more algorithms to select a subset of the reference patient data sets, e.g., based on similarity to the patient data set 108 and/or treatment outcome of the corresponding reference patient. For example, the data analysis module 116 can identify one or more similar patient data sets in the reference patient data sets, and then select a subset of the similar patient data sets based on whether the similar patient data set includes data indicative of a favorable or desired treatment outcome. The outcome data can include data representing one or more outcome parameters, such as corrected anatomical metrics, presence of fusion, HRQL, activity level, complications, recovery times, efficacy, mortality, or follow-up surgeries. As described in further detail below, in some embodiments, the data analysis module 116 calculates an outcome score by assigning values to each outcome parameter. A patient can be considered to have a favorable outcome if the outcome score is above, below, or at a specified threshold value.

In some embodiments, the data analysis module 116 selects a subset of the reference patient data sets based at least in part on user input (e.g., from a clinician, surgeon, physician, healthcare provider). For example, the user input can be used in identifying similar patient data sets. In some embodiments, weighting of similarity and/or outcome parameters can be selected by a healthcare provider or physician to adjust the similarity and/or outcome score based on clinician input. In further embodiments, the healthcare provider or physician can select the set of similarity and/or outcome parameters (or define new similarity and/or outcome parameters) used to generate the similarity and/or outcome score, respectively.

In some embodiments, the data analysis module 116 includes one or more algorithms used to select a set or subset of the reference patient data sets based on criteria other than patient parameters. For example, the one or more algorithms can be used to select the subset based on healthcare provider parameters (e.g., based on healthcare provider ranking/scores such as hospital/physician expertise, number of procedures performed, hospital ranking, etc.) and/or healthcare resource parameters (e.g., diagnostic equipment, facilities, surgical equipment such as surgical robots), or other non-patient related information that can be used to predict outcomes and risk profiles for procedures for the present healthcare provider. For example, reference patient data sets with images captured from similar diagnostic equipment can be aggregated to reduce or limit irregularities due to variation between diagnostic equipment. Additionally, patient-specific treatment plans can be developed for a particular health-care provider using data from similar healthcare providers (e.g., healthcare providers with traditionally similar outcomes, physician expertise, surgical teams, etc.). In some embodiments, reference healthcare provider data sets, hospital data sets, physician data sets, surgical team data sets, post-treatment data set, and other data sets can be utilized. By way of example, a patient-specific treatment plan to perform a battlefield surgery can be based on reference patient data from similar battlefield surgeries and/or datasets associated with battlefield surgeries. In another example, the patient-specific treatment plan can be generated based on available robotic surgical systems. The reference patient data sets can be selected based on patients that have been operated on using comparable robotic surgical systems under similar conditions (e.g., size and capabilities of surgical teams, hospital resources, etc.).

The treatment planning module 118 is configured with one or more algorithms to generate at least one treatment plan (e.g., pre-operative plans, surgical plans, post-operative plans etc.) based on the output from the data analysis module 116. In some embodiments, the treatment planning module 118 is configured to develop and/or implement at least one predictive model for generating the patient-specific treatment plan, also known as a "prescriptive model." The predictive model(s) can be developed using clinical knowledge, statistics, machine learning, AI, neural networks, or the like. In some embodiments, the output from the data analysis module 116 is analyzed (e.g., using statistics, machine learning, neural networks, AI) to identify correlations between data sets, patient parameters, healthcare provider parameters, healthcare resource parameters, treatment procedures, medical device designs, and/or treatment outcomes. These correlations can be used to develop at least one predictive model that predicts the likelihood that a treatment plan will produce a favorable outcome for the particular patient. The predictive model(s) can be validated, e.g., by inputting data into the model(s) and comparing the output of the model to the expected output.

In some embodiments, the treatment planning module 118 is configured to generate the treatment plan based on previous treatment data from reference patients. For example, the treatment planning module 118 can receive a selected subset of reference patient data sets and/or similar patient data sets from the data analysis module 116, and determine or identify treatment data from the selected subset. The treatment data can include, for example, treatment procedure data (e.g., surgical procedure or intervention data) and/or medical device design data (e.g., implant design data) that are associated with favorable or desired treatment outcomes for the corresponding patient. The treatment planning module 118 can analyze the treatment procedure data and/or medical device design data to determine an optimal treatment protocol for the patient to be treated. For example, the treatment procedures and/or medical device designs can be assigned values and aggregated to produce a treatment score. The patient-specific treatment plan can be determined by selecting treatment plan(s), or one or more aspects thereof, based on the score (e.g., higher or highest score; lower or lowest score; score that is above, below, or at a specified threshold value).

Alternatively or in combination, the treatment planning module 118 can generate the treatment plan based on correlations between data sets. For example, the treatment planning module 118 can correlate treatment procedure data and/or medical device design data from similar patients with favorable outcomes (e.g., as identified by the data analysis module 116). Correlation analysis can include transforming correlation coefficient values to values or scores. The values/scores can be aggregated, filtered, or otherwise analyzed to determine one or more statistical significances. These correlations can be used to determine treatment procedure(s) and/or medical device design(s) that are optimal or likely to produce a favorable outcome for the patient to be treated.

Alternatively or in combination, the treatment planning module 118 can generate the treatment plan using one or more AI techniques. AI techniques can be used to develop computing systems capable of simulating aspects of human intelligence, e.g., learning, reasoning, planning, problem solving, decision making, etc. AI techniques can include, but are not limited to, case-based reasoning, rule-based systems, artificial neural networks, decision trees, support vector machines, regression analysis, Bayesian networks (e.g., naïve Bayes classifiers), genetic algorithms, cellular automata, fuzzy logic systems, multi-agent systems, swarm intelligence, data mining, machine learning (e.g., supervised learning, unsupervised learning, reinforcement learning), and hybrid systems.

In some embodiments, the treatment planning module 118 generates the treatment plan using one or more trained machine learning models. Various types of machine learning models, algorithms, and techniques are suitable for use with the present technology. In some embodiments, the machine learning model is initially trained on a training data set, which is a set of examples used to fit the parameters (e.g., weights of connections between "neurons" in artificial neural networks) of the model. For example, the training data set can include any of the reference data stored in database 110, such as a plurality of reference patient data sets or a selected subset thereof (e.g., a plurality of similar patient data sets).

In some embodiments, the machine learning model (e.g., a neural network or a naïve Bayes classifier) may be trained on the training data set using a supervised learning method (e.g., gradient descent or stochastic gradient descent). The training dataset can include pairs of generated "input vectors" with the associated corresponding "answer vector" (commonly denoted as the target). The current model is run with the training data set and produces a result, which is then compared with the target, for each input vector in the training data set. Based on the result of the comparison and the specific learning algorithm being used, the parameters of the model are adjusted. The model fitting can include both variable selection and parameter estimation. The fitted model can be used to predict the responses for the observations in a second data set called the validation data set. The validation data set can provide an unbiased evaluation of a model fit on the training data set while tuning the model parameters. Validation data sets can be used for regularization by early stopping, e.g., by stopping training when the error on the validation data set increases, as this may be a sign of overfitting to the training data set. In some embodiments, the error of the validation data set error can fluctuate during training, such that ad-hoc rules may be used to decide when overfitting has truly begun. Finally, a test data set can be used to provide an unbiased evaluation of a final model fit on the training data set.

To generate a treatment plan, the patient data set 108 can be input into the trained machine learning model(s). Additional data, such as the selected subset of reference patient data sets and/or similar patient data sets, and/or treatment data from the selected subset, can also be input into the trained machine learning model(s). The trained machine learning model(s) can then calculate whether various candidate treatment procedures and/or medical device designs are likely to produce a favorable outcome for the patient. Based on these calculations, the trained machine learning model(s) can select at least one treatment plan for the patient. In embodiments where multiple trained machine learning models are used, the models can be run sequentially or concurrently to compare outcomes and can be periodically updated using training data sets. The treatment planning module 118 can use one or more of the machine learning models based the model's predicted accuracy score.

The patient-specific treatment plan generated by the treatment planning module 118 can include at least one patient-specific treatment procedure (e.g., a surgical procedure or intervention) and/or at least one patient-specific medical device (e.g., an implant or implant delivery instrument). A patient-specific treatment plan can include an entire surgical procedure or portions thereof. Additionally, one or more patient-specific medical devices can be specifically selected or designed for the corresponding surgical procedure, thus allowing for the various components of the patient-specific technology to be used in combination to treat the patient.

In some embodiments, the patient-specific treatment procedure includes an orthopedic surgery procedure, such as spinal surgery, hip surgery, knee surgery, jaw surgery, hand surgery, shoulder surgery, elbow surgery, total joint reconstruction (arthroplasty), skull reconstruction, foot surgery, or ankle surgery. Spinal surgery can include spinal fusion surgery, such as posterior lumbar interbody fusion (PLIF), anterior lumbar interbody fusion (ALIF), transverse or transforaminal lumbar interbody fusion (TLIF), lateral lumbar interbody fusion (LLIF), direct lateral lumbar interbody fusion (DLIF), extreme lateral lumbar interbody fusion (XLIF), and/or sacroiliac joint fusion (SIJF). In some embodiments, the patient-specific treatment procedure includes descriptions of and/or instructions for performing one or more aspects of a patient-specific surgical procedure. For example, the patient-specific surgical procedure can include one or more of a surgical approach, a corrective maneuver, a bony resection, or implant placement.

In some embodiments, the patient-specific medical device design includes a design for an orthopedic implant and/or a design for an instrument for delivering the orthopedic implant. Examples of such orthopedic implants include, but are not limited to, screws (e.g., bone screws, spinal screws, pedicle screws, facet screws), interbody implant devices (e.g., intervertebral implants), cages, plates, rods, disks, fusion devices, spacers, rods, expandable devices, stents, brackets, ties, scaffolds, fixation device, anchors, nuts, bolts, rivets, connectors, tethers, fasteners, joint replacements, hip implants, or the like. Examples of such instruments include, but are not limited to, screw guides, cannulas, ports, catheters, insertion tools, or the like.

A patient-specific medical device design can include data representing one or more of physical properties (e.g., size, shape, volume, material, mass, weight), mechanical properties (e.g., stiffness, strength, modulus, hardness), and/or biological properties (e.g., osteo-integration, cellular adhesion, anti-bacterial properties, anti-viral properties) of a corresponding medical device. For example, a design for an orthopedic implant can include implant shape, size, material, and/or effective stiffness (e.g., lattice density, number of struts, location of struts, etc.). In some embodiments, the generated patient-specific medical device design is a design for an entire device. In other embodiments, the generated design is for one or more components of a device, rather than the entire device. In these and other embodiments, the generated design is for one or more patient-specific device components that can be used with standard, off-the-shelf components. For example, in the context of a spinal surgery procedure, a pedicle screw kit can include both standard components and patient-specific customized components. In some embodiments, the generated design is for a patient-specific medical device that can be used with a standard, off-the-shelf delivery instrument. For example, the implants (e.g., screws, screw holders, rods) can be designed and manufactured for the patient, while the instruments for delivering the implants can be standard instruments. This approach allows the components that are implanted to be designed and manufactured based on the patient's anatomy and/or surgeon's preferences to enhance treatment. The patient-specificity of the devices described herein is expected to improve delivery of these device into the patient's body, placement of these devices at the treatment site, and/or interaction of these devices with the patient's anatomy.

In embodiments where the patient-specific treatment plan includes a surgical procedure to implant a medical device, the treatment planning module 118 can also store various types of implant surgery information, such as implant parameters (e.g., types, dimensions), availability of implants, aspects of a pre-operative plan (e.g., initial implant configuration, detection and measurement of the patient's anatomy, etc.), FDA requirements for implants (e.g., specific implant parameters and/or characteristics for compliance with FDA regulations), or the like. In some embodiments, the treatment planning module 118 can convert the implant surgery information into formats useable for machine-learning based models and algorithms. For example, the implant surgery information can be tagged with particular identifiers for formulas or can be converted into numerical representations suitable for supplying to the trained machine learning model(s). The treatment planning module 118 can also store information regarding the patient's anatomy, such as two- or three-dimensional images or models of the anatomy, and/or information regarding the biology, geometry, and/or mechanical properties of the anatomy. The anatomy information can be used to inform implant design and/or placement.

The treatment plan(s) generated by the treatment planning module 118 can be transmitted via the communication network 104 to the client computing device 102 for output to a user (e.g., clinician, surgeon, healthcare provider, patient). In some embodiments, the client computing device 102 includes or is operably coupled to a display 122 for outputting the treatment plan(s). The display 122 can include a graphical user interface (GUI) for visually depicting various aspects of the treatment plan(s). For example, the display 122 can show various aspects of a surgical procedure to be performed on the patient, such as the surgical approach, treatment levels, corrective maneuvers, tissue resection, and/or implant placement. To facilitate visualization, a virtual model of the surgical procedure can be displayed. As another example, the display 122 can show a design for a medical device to be implanted in the patient, such as a two- or three-dimensional model of the device design. The display 122 can also show patient information, such as two- or three-dimensional images or models of the patient's anatomy where the surgical procedure is to be performed and/or where the device is to be implanted. The client computing device 102 can further include one or more user input devices (not shown) allowing the user to modify, select, approve, and/or reject the displayed treatment plan(s).

In some embodiments, the medical device design(s) generated by the treatment planning module 118 can be transmitted from the client computing device 102 and/or server 106 to a manufacturing system 124 for manufacturing a corresponding medical device. The manufacturing system 124 can be located on site or off site. On-site manufacturing can reduce the number of sessions with a patient and/or the time to be able to perform the surgery whereas off-site manufacturing can be useful make the complex devices.

Off-site manufacturing facilities can have specialized manufacturing equipment. In some embodiments, more complicated device components can be manufactured off site, while simpler device components can be manufactured on site.

Various types of manufacturing systems are suitable for use in accordance with the embodiments herein. For example, the manufacturing system 124 can be configured for additive manufacturing, such as three-dimensional (3D) printing, stereolithography (SLA), digital light processing (DLP), fused deposition modeling (FDM), selective laser sintering (SLS), selective laser melting (SLM), selective heat sintering (SHM), electronic beam melting (EBM), laminated object manufacturing (LOM), powder bed printing (PP), thermoplastic printing, direct material deposition (DMD), inkjet photo resin printing, or like technologies, or combination thereof. Alternatively or in combination, the manufacturing system 124 can be configured for subtractive (traditional) manufacturing, such as CNC machining, electrical discharge machining (EDM), grinding, laser cutting, water jet machining, manual machining (e.g., milling, lathe/turning), or like technologies, or combinations thereof. The manufacturing system 124 can manufacture one or more patient-specific medical devices based on fabrication instructions or data (e.g., CAD data, 3D data, digital blueprints, stereolithography data, or other data suitable for the various manufacturing technologies described herein). Different components of the system 100 can generate at least a portion of the manufacturing data used by the manufacturing system 124. The manufacturing data can include, without limitation, fabrication instructions (e.g., programs executable by additive manufacturing equipment, subtractive manufacturing equipment, etc.), 3D data, CAD data (e.g., CAD files), CAM data (e.g., CAM files), path data (e.g., print head paths, tool paths, etc.), material data, tolerance data, surface finish data (e.g., surface roughness data), regulatory data (e.g., FDA requirements, reimbursement data, etc.), or the like. The manufacturing system 124 can analyze the manufacturability of the implant design based on the received manufacturing data. The implant design can be finalized by altering geometries, surfaces, etc. and then generating manufacturing instructions. In some embodiments, the server 106 generates at least a portion of the manufacturing data, which is transmitted to the manufacturing system 124.

The manufacturing system 124 can generate CAM data, print data (e.g., powder bed print data, thermoplastic print data, photo resin data, etc.), or the like and can include additive manufacturing equipment, subtractive manufacturing equipment, thermal processing equipment, or the like. The additive manufacturing equipment can be 3D printers, stereolithography devices, digital light processing devices, fused deposition modeling devices, selective laser sintering devices, selective laser melting devices, electronic beam melting devices, laminated object manufacturing devices, powder bed printers, thermoplastic printers, direct material deposition devices, or inkjet photo resin printers, or like technologies. The subtractive manufacturing equipment can be CNC machines, electrical discharge machines, grinders, laser cutters, water jet machines, manual machines (e.g., milling machines, lathes, etc.), or like technologies. Both additive and subtractive techniques can be used to produce implants with complex geometries, surface finishes, material properties, etc. The generated fabrication instructions can be configured to cause the manufacturing system 124 to manufacture the patient-specific orthopedic implant that matches or is therapeutically the same as the patient-specific design. In some embodiments, the patient-specific medical device can include features, materials, and designs shared across designs to simplify manufacturing. For example, deployable patient-specific medical devices for different patients can have similar internal deployment mechanisms but have different deployed configurations. In some embodiments, the components of the patient-specific medical devices are selected from a set of available pre-fabricated components and the selected pre-fabricated components can be modified based on the fabrication instructions or data.

The treatment plans described herein can be performed by a surgeon, a surgical robot, or a combination thereof, thus allowing for treatment flexibility. In some embodiments, the surgical procedure can be performed entirely by a surgeon, entirely by a surgical robot, or a combination thereof. For example, one step of a surgical procedure can be manually performed by a surgeon and another step of the procedure can be performed by a surgical robot. In some embodiments the treatment planning module 118 generates control instructions configured to cause a surgical robot (e.g., robotic surgery systems, navigation systems, etc.) to partially or fully perform a surgical procedure. The control instructions can be transmitted to the robotic apparatus by the client computing device 102 and/or the server 106.

Following the treatment of the patient in accordance with the treatment plan, treatment progress can be monitored over one or more time periods to update the data analysis module 116 and/or treatment planning module 118. Post-treatment data can be added to the reference data stored in the database 110. The post-treatment data can be used to train machine learning models for developing patient-specific treatment plans, patient-specific medical devices, or combinations thereof.

It shall be appreciated that the components of the system 100 can be configured in many different ways. For example, in alternative embodiments, the database 110, the data analysis module 116 and/or the treatment planning module 118 can be components of the client computing device 102, rather than the server 106. As another example, the database 110 the data analysis module 116, and/or the treatment planning module 118 can be located across a plurality of different servers, computing systems, or other types of cloud-computing resources, rather than at a single server 106 or client computing device 102.

Additionally, in some embodiments, the system 100 can be operational with numerous other computing system environments or configurations. Examples of computing systems, environments, and/or configurations that may be suitable for use with the technology include, but are not limited to, personal computers, server computers, handheld or laptop devices, cellular telephones, wearable electronics, tablet devices, multiprocessor systems, microprocessor-based systems, programmable consumer electronics, network PCs, minicomputers, mainframe computers, distributed computing environments that include any of the above systems or devices, or the like.

Figure 1B:
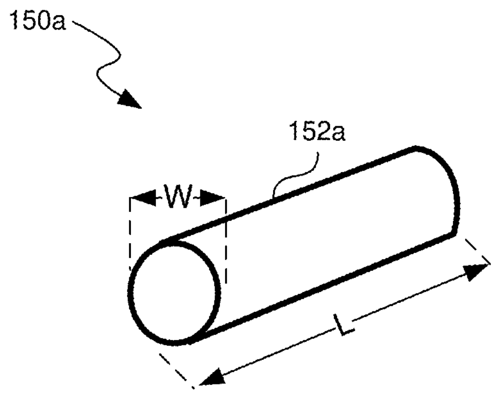
FIGS. 1B-1D are schematic illustrations of patient-specific sacroiliac joint implants configured in accordance with embodiments of the present technology.

FIG. 1B illustrates an implant 150*a* designed by the system 100 in accordance with embodiments of the present technology. The implant 150*a* can be a sacroiliac joint implant configured to be implanted at a target location at least partially within, through, and/or near a patient's sacroiliac joint, and can include one or more patient-specific features. In the illustrated embodiment, for example, the implant 150*a* includes an elongate body 152*a* having a length L and a width W. The length L and width W can be selected by the system 100, e.g., based on patient data corresponding to the specific anatomy and/or geometry of the patient's sacrum, ilium, and/or sacroiliac joint, as described previously. Additionally, or alternatively, the cross-sectional shape of the implant 150*a* can be selected by the system 100 and/or based on patient data. For example, although depicted as having a circular cross-sectional shape in FIG. 1B, in other embodiments the implant 150*a* can have a triangular, square, rectangular, pentagonal, hexagonal, or any other suitable cross-sectional shape.

Figure 1C:
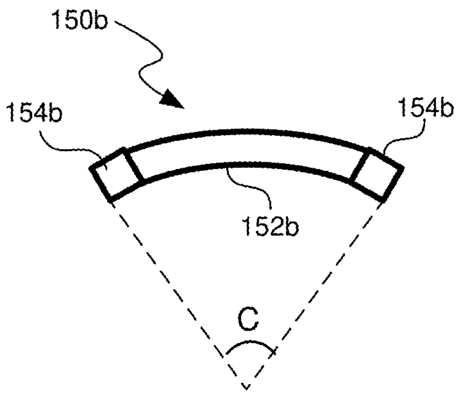

FIG. 1C illustrates another implant 150*b* that can be designed by the system 100. The implant 150*b* includes an elongate curved body 152*b* and one or more anchors or attachment points 154*b*. Each of the attachment points 154*b* can include one or more screws, rods, pins, anchors, etc., and/or can be configured to receive one or more screws, rods, pins, anchors, etc. The implant 150*b* can be a sacroiliac joint implant designed to be implanted at a target location at least partially within, through, and/or near a patient's sacroiliac joint. The design of the implant 150*b* can include one or more patient-specific aspects or features. For example, the body 152*b* can have contouring or curvature C designed and/or otherwise configured to correspond to the curvature (e.g., contour, geometry, surface, topology, etc.) of a patient's sacrum, ilium, and/or sacroiliac joint. Additionally, the position (e.g., location, spacing, arrangement, etc.) and/or configuration of each the attachment points 154*b* can correspond to a location at least partially within, through, at, on, and/or proximate to the target site, e.g., where the implant 150*b* can be attached (e.g., couple, anchored, fused, etc.) to the patient's sacrum, ilium, and/or sacroiliac joint.

Figure 1D:
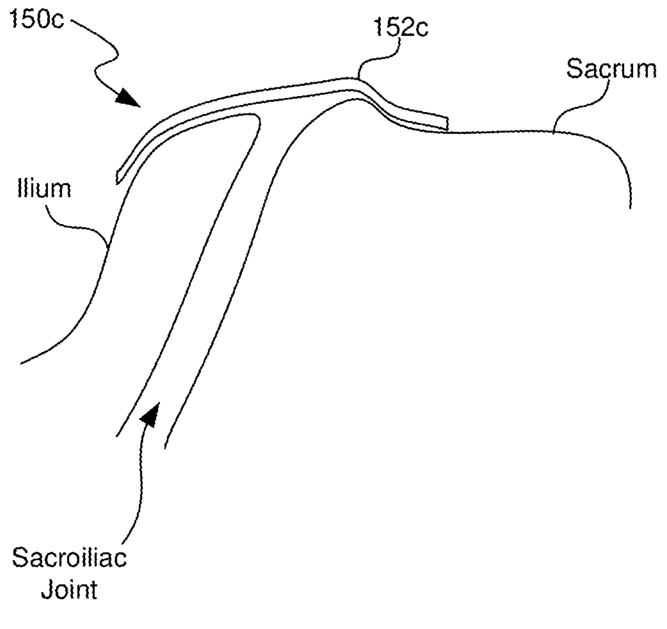

FIG. 1D illustrates another implant 150*c* that can be designed by the system 100. Specifically, the implant 150*c* can be designed and/or otherwise configured to match the specific shape, curvature, and/or contouring of a patient's sacrum, ilium, and/or sacroiliac joint. For example, in the embodiment illustrated in FIG. 1D, the implant 150*c* includes an elongate body 152*c* configured (e.g., shaped, curved, contoured, etc.) to match the ilium, sacrum, and/or sacroiliac joint. Although illustrated as being positioned external to the ilium, sacrum, and/or sacroiliac joint in FIG. 1D, in other embodiments the implant can be configured for at least partial insertion within the ilium, sacrum, and/or sacroiliac joint. For example, the implant can be or include one or more rods, pins, screws, etc., each of which can be designed to have a shape, curvature, and/or contouring configured to correspond to the shape, curvature, and/or contouring of the patient's ilium, sacrum, and/or sacroiliac joint. In at least some embodiments, any of the implants 150*a, b*, and/or c, can be configured to have a lateral surface or surfaces that conform to the lateral surfaces of the adjacent anatomy, particularly the lateral or inferior aspect of the ilium.

Figure 2:
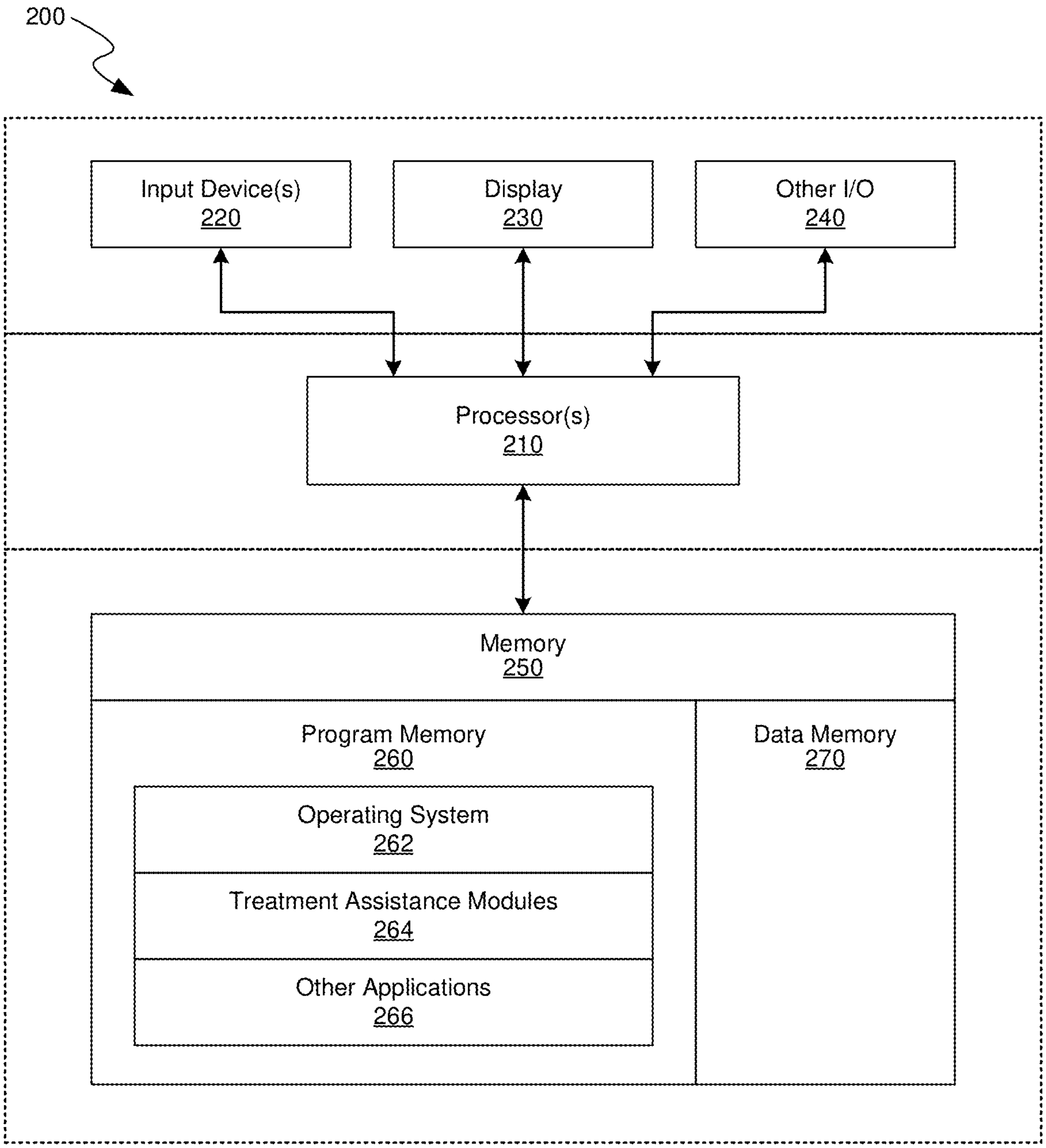
FIG. 2 illustrates a computing device suitable for use in connection with the system of FIG. 1A, configured in accordance with embodiments of the present technology.

FIG. 2 illustrates a computing device 200 suitable for use in connection with the system 100 of FIG. 1A, in accordance with embodiments of the present technology. The computing device 200 can be incorporated in various components of the system 100 of FIG. 1A, such as the client computing device 102 or the server 106. The computing device 200 includes one or more processors 210 (e.g., CPU(s), GPU(s), HPU(s), etc.). The processor(s) 210 can be a single processing unit or multiple processing units in a device or distributed across multiple devices. The processor(s) 210 can be coupled to other hardware devices, for example, with the use of a bus, such as a PCI bus or SCSI bus. The processor(s) 210 can be configured to execute one more computer-readable program instructions, such as program instructions to carry out of any of the methods described herein and/or one or more blocks/steps thereof.

The computing device 200 can include one or more input devices 220 that provide input to the processor(s) 210, e.g., to notify it of actions from a user of the device 200. The actions can be mediated by a hardware controller that interprets the signals received from the input device and communicates the information to the processor(s) 210 using a communication protocol. Input device(s) 220 can include, for example, a mouse, a keyboard, a touchscreen, an infrared sensor, a touchpad, a wearable input device, a camera- or image-based input device, a microphone, or other user input devices.

The computing device 200 can include a display 230 used to display various types of output, such as text, models, virtual procedures, surgical plans, implants, graphics, and/or images (e.g., images with voxels indicating radiodensity units or Hounsfield units representing the density of the tissue at a location). In some embodiments, the display 230 provides graphical and textual visual feedback to a user. The processor(s) 210 can communicate with the display 230 via a hardware controller for devices. In some embodiments, the display 230 includes the input device(s) 220 as part of the display 230, such as when the input device(s) 220 include a touchscreen or is equipped with an eye direction monitoring system. In alternative embodiments, the display 230 is separate from the input device(s) 220. Examples of display devices include an LCD display screen, an LED display screen, a projected, holographic, or augmented reality display (e.g., a heads-up display device or a head-mounted device), and so on.

Optionally, other I/O devices 240 can also be coupled to the processor(s) 210, such as a network card, video card, audio card, USB, firewire or other external device, camera, printer, speakers, CD-ROM drive, DVD drive, disk drive, or Blu-Ray device. Other I/O devices 240 can also include input ports for information from directly connected medical equipment such as imaging apparatuses, including MRI machines, X-Ray machines, CT machines, etc. Other I/O devices 240 can further include input ports for receiving data from these types of machines from other sources, such as across a network or from previously captured data, for example, stored in a database.

In some embodiments, the computing device 200 also includes a communication device (not shown) capable of communicating wirelessly or wire-based with a network node. The communication device can communicate with another device or a server through a network using, for example, TCP/IP protocols. The computing device 200 can utilize the communication device to distribute operations across multiple network devices, including imaging equipment, manufacturing equipment, etc.

The computing device 200 can include memory 250, which can be in a single device or distributed across multiple devices. Memory 250 includes one or more of various hardware devices for volatile and non-volatile storage, and can include both read-only and writable memory. For example, a memory can comprise random access memory (RAM), various caches, CPU registers, read-only memory (ROM), and writable non-volatile memory, such as flash memory, hard drives, floppy disks, CDs, DVDs, magnetic storage devices, tape drives, device buffers, and so forth. A memory is not a propagating signal divorced from underlying hardware; a memory is thus non-transitory. In some embodiments, the memory 250 is a non-transitory computer-readable storage medium that stores, for example, programs, software, data, or the like. In some embodiments, memory 250 can include program memory 260 that stores programs and software, such as an operating system 262, one or more treatment assistance modules 264, and other application programs 266. The treatment assistance module(s) 264 can include one or more modules configured to perform the various methods described herein (e.g., the data analysis module 116 and/or treatment planning module 118 described with respect to FIG. 1A). Memory 250 can also include data memory 270 that can include, e.g., reference data, configuration data, settings, user options or preferences, etc., which can be provided to the program memory 260 or any other element of the computing device 200.

Figure 3:
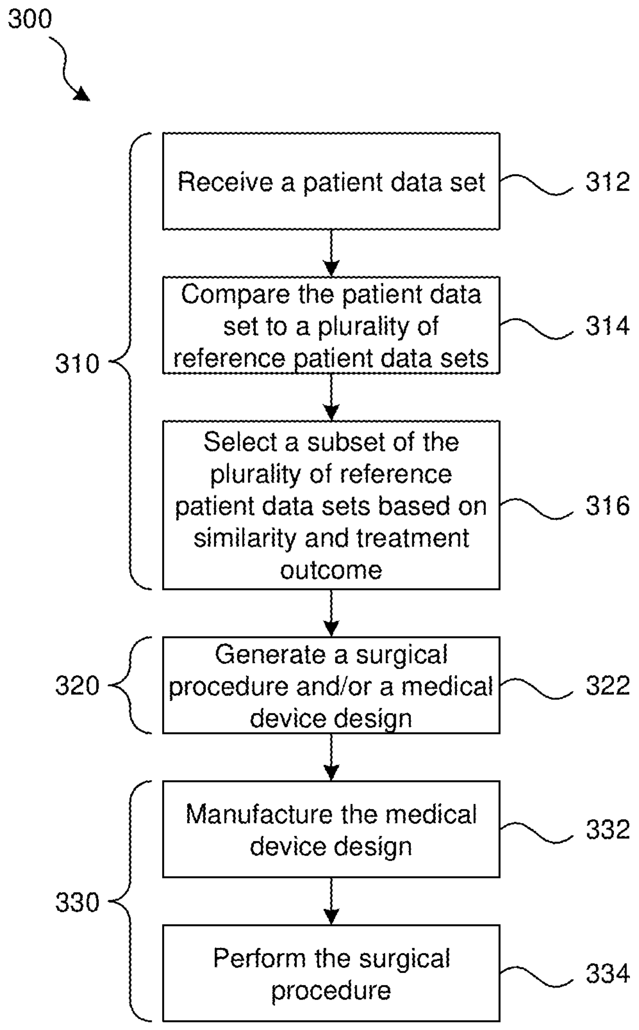
FIG. 3 is a flow diagram illustrating a method for providing patient-specific medical care, in accordance with embodiments of the present technology.

FIG. 3 is a flow diagram illustrating a method 300 for providing patient-specific medical care, in accordance with embodiments of the present technology. The method 300 can include a data phase 310, a modeling phase 320, and an execution phase 330. The data phase 310 can include collecting data of a patient to be treated (e.g., pathology data), and comparing the patient data to reference data (e.g., prior patient data such as pathology, surgical, and/or outcome data). For example, a patient data set can be received (block 312). The patient data set can be compared to a plurality of reference patient data sets (block 314), e.g., in order to identify one or more similar patient data sets in the plurality of reference patient data sets. Each of the plurality of reference patient data sets can include data representing one or more of age, gender, BMI, lumbar lordosis, Cobb angle(s), pelvic incidence, disc height, segment flexibility, bone quality, rotational displacement, sacroiliac joint anatomy (e.g., dimension(s), curvature, shape, topology, etc.), and/or treatment level of the spine.

A subset of the plurality of reference patient data sets can be selected (block 316), e.g., based on similarity to the patient data set and/or treatment outcomes of the corresponding reference patients. For example, a similarity score can be generated for each reference patient data set, based on the comparison of the patient data set and the reference patient data set. The similarity score can represent a statistical correlation between the patient data and the reference patient data set. One or more similar patient data sets can be identified based, at least partly, on the similarity score.

In some embodiments, each patient data set of the selected subset includes and/or is associated with data indicative of a favorable treatment outcome (e.g., a favorable treatment outcome based on a single target outcome, aggregate outcome score, outcome thresholding). The data can include, for example, data representing one or more of corrected anatomical metrics, presence of fusion, health related quality of life, activity level, or complications. In some embodiments, the data is or includes an outcome score, which can be calculated based on a single target outcome, an aggregate outcome, and/or an outcome threshold.

Optionally, the data analysis phase 310 can include identifying or determining, for at least one patient data set of the selected subset (e.g., for at least one similar patient data set), surgical procedure data and/or medical device design data associated with the favorable treatment outcome. The surgical procedure data can include data representing one or more of a surgical approach, a corrective maneuver, a bony resection, and/or implant placement. The at least one medical device design can include data representing one or more of physical properties, mechanical properties, and/or biological properties of a corresponding medical device. In some embodiments, the at least one patient-specific medical device design includes a design for an implant and/or an implant delivery instrument. This can include, for example, a sacroiliac joint implant, such as the implants 150*a*-*c* of FIGS. 1A-1C, and/or a sacroiliac join implant delivery instrument configured to deliver and/or position a sacroiliac joint implant in a transjoint and/or an intrajoint space.

In the modeling phase 320, a surgical procedure and/or medical device design is generated (block 322). The generating step can include developing at least one predictive model based on the patient data set and/or selected subset of reference patient data sets (e.g., using statistics, machine learning, neural networks, AI, or the like). The predictive model can be configured to generate the surgical procedure and/or medical device design.

In some embodiments, the predictive model includes one or more trained machine learning models that generate, at least partly, the surgical procedure and/or medical device design. For example, the trained machine learning model(s) can determine a plurality of candidate surgical procedures and/or medical device designs for treating the patient. Each surgical procedure can be associated with a corresponding medical device design. In some embodiments, the surgical procedures and/or medical device designs are determined based on surgical procedure data and/or medical device design data associated with favorable outcomes, as previously described with respect to the data analysis phase 310. For each surgical procedure and/or corresponding medical device design, the trained machine learning model(s) can calculate a probability of achieving a target outcome (e.g., favorable or desired outcome) for the patient. The trained machine learning model(s) can then select at least one surgical procedure and/or corresponding medical device design based, at least partly, on the calculated probabilities.

The execution phase 330 can include manufacturing the medical device design (block 332). In some embodiments, the medical device design is manufactured by a manufacturing system configured to perform one or more of additive manufacturing, 3D printing, stereolithography, digital light processing, fused deposition modeling, selective laser sintering, selective laser melting, electronic beam melting, laminated object manufacturing, powder bed printing, thermoplastic printing, direct material deposition, or inkjet photo resin printing. The execution phase 330 can optionally include generating fabrication instructions configured to cause the manufacturing system to manufacture a medical device having the medical device design.

The execution phase 330 can include performing the surgical procedure (block 334). The surgical procedure can involve implanting a medical device having the medical device design into the patient. The surgical procedure can be performed manually (e.g., by a practitioner or physician), by a surgical robot, and/or a combination thereof. In embodiments where the surgical procedure is performed by a surgical robot, the execution phase 330 can include generating control instructions configured to cause the surgical robot to perform, at least partly, the patient-specific surgical procedure.

The method 300 can be implemented and performed in various ways. In some embodiments, one or more steps of the method 300 (e.g., the data phase 310 and/or the modeling phase 320) can be implemented as computer-readable instructions stored in memory and executable by one or more processors of any of the computing devices and systems described herein (e.g., the system 100), or a component thereof (e.g., the client computing device 102 and/or the server 106). Alternatively, one or more steps of the method 300 (e.g., the execution phase 330) can be performed by a healthcare provider (e.g., physician, surgeon), a robotic apparatus (e.g., a surgical robot), a manufacturing system (e.g., manufacturing system 124), or a combination thereof. In some embodiments, one or more steps of the method 300 are omitted (e.g., the execution phase 330).

Figure 4A:
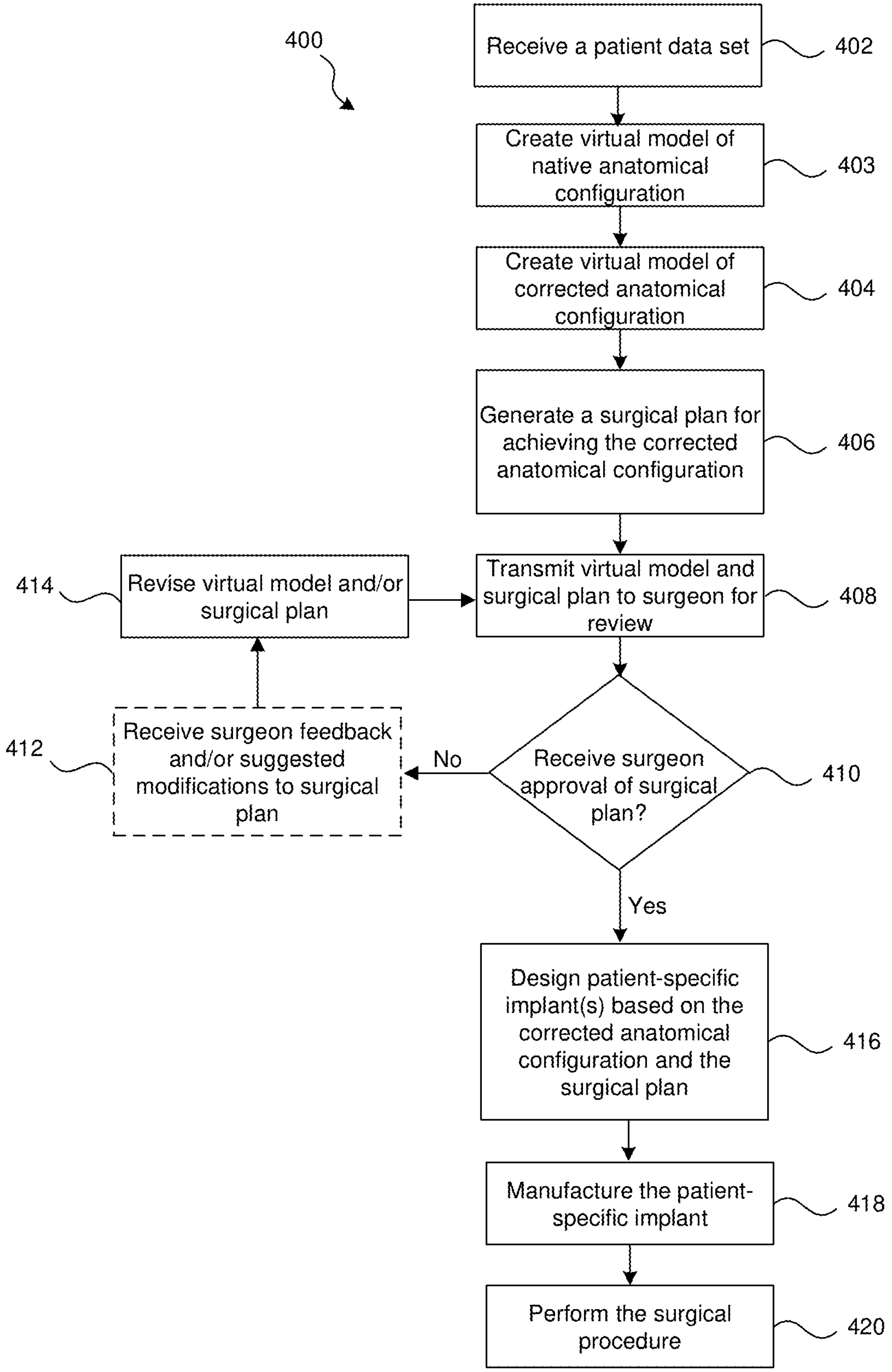
FIG. 4A is a flow diagram illustrating another method for providing patient-specific medical care, in accordance with embodiments of the present technology.

FIG. 4A is a flow diagram illustrating a method 400 for providing patient-specific medical care, in accordance with embodiments of the present technology. The method 400 can begin in step 402 by receiving a patient data set for a particular patient in need of medical treatment. The patient data set can be generally similar to or the same as the patient data set 108 of FIG. 1A, and can include data representative of the patient's condition, anatomy, pathology, symptoms, medical history, preferences, and/or any other information or parameters relevant to the patient. For example, the patient data set can include surgical intervention data, treatment outcome data, progress data (e.g., surgeon notes), patient feedback (e.g., feedback acquired using quality of life questionnaires, surveys), clinical data, patient information (e.g., demographics, sex, age, height, weight, type of pathology, occupation, activity level, tissue information, health rating, comorbidities, health related quality of life (HRQL)), vital signs, diagnostic results, medication information, allergies, diagnostic equipment information (e.g., manufacturer, model number, specifications, user-selected settings/configurations, etc.), and/or the like. The patient data set can also include image data, such as camera images, Magnetic Resonance Imaging (MRI) images, ultrasound images, Computerized Aided Tomography (CAT) scan images, Positron Emission Tomography (PET) images, X-Ray images, and/or the like. In some embodiments, the patient data set includes data representing one or more of patient identification number (ID), age, gender, body mass index (BMI), lumbar lordosis, Cobb angle(s), pelvic incidence, disc height, segment flexibility, bone quality, rotational displacement, sacroiliac joint anatomy (e.g., dimension(s), property(s), curvature, shape, topology, etc.), pain data, and/or treatment level of the spine. The patient data set can be received at a server, computing device, and/or another computing system. For example, in some embodiments the patient data set can be received by the server 106 shown in FIG. 1A and/or the computing system 506 described below with respect to FIG. 5. In some embodiments, the computing system that receives the patient data set in step 402 also stores one or more software modules (e.g., the data analysis module 116 and/or the treatment planning module 118, shown in FIG. 1A, and/or additional software modules for performing various operations of the method 400). Additional details for collecting and receiving the patient data set are described below with respect to FIG. 5.

In some embodiments, the received patient data set can include disease metrics such as lumbar lordosis, Cobb angles, pain data, coronal parameters (e.g., coronal balance, global coronal balance, coronal pelvic tilt, etc.), sagittal parameters (e.g., pelvic incidence, sacral slope, thoracic kyphosis, etc.) and/or pelvic parameters. The disease metrics can include micro-measurements (e.g., metrics associated with specific or individual segments of the patient's spine) and/or macro-measurements (e.g., metrics associated with multiple segments of the patient's spine). In some embodiments, the disease metrics are not included in the patient data set, and the method 400 includes determining (e.g., automatically determining) one or more of the disease metrics based on the patient image data, as described below.

Once the patient data set is received in step 402, the method 400 can continue in step 403 by creating a virtual model of the patient's native anatomical configuration (also referred to as "pre-operative anatomical configuration"). The virtual model can be based on the image data included in the patient data set received in step 402. For example, the same computing system that received the patient data set in step 402 can analyze the image data in the patient data set to generate a virtual model of the patient's native anatomical configuration. The virtual model can be a two- or three-dimensional visual representation of the patient's native anatomy. The virtual model can include one or more regions of interest, and may include some or all of the patient's anatomy within the regions of interest (e.g., any combination of tissue types including, but not limited to, bony structures, cartilage, soft tissue, vascular tissue, nervous tissue, etc.). As a non-limiting example, the virtual model can include a visual representation of the patient's spinal cord region, including at least part or all of the sacrum, lumbar region, thoracic region, and/or cervical region. In another non-limiting example, the virtual model can include a visual representation of a patient's pelvic region, including at least part or all of the sacrum, ilium, and/or one or both of the sacroiliac joints. In some embodiments, the virtual model includes soft tissue, cartilage, and/or other non-bony structures. In other embodiments, the virtual model only includes the patient's bony structures. Examples of virtual models of native anatomical configurations are described below with respect to FIGS. 6A-6B. In some embodiments, the method 400 can optionally omit creating a virtual model of the patient's native anatomy in step 403, and proceed directly from step 402 to step 404.

In some embodiments, the computing system that generated the virtual model in step 402 can also determine (e.g., automatically determine or measure) one or more disease metrics of the patient based on the virtual model. For example, the computing system may analyze the virtual model to determine the patient's pre-operative lumbar lordosis, Cobb angles, pain data, coronal parameters (e.g., coronal balance, global coronal balance, coronal pelvic tilt, etc.), sagittal parameters (e.g., pelvic incidence, sacral slope, thoracic kyphosis, etc.) and/or pelvic parameters. The disease metrics can include micro-measurements (e.g., metrics associated with specific or individual segments of the patient's spine) and/or macro-measurements (e.g., metrics associated with multiple segments of the patient's spine).

The method 400 can continue in step 404 by creating a virtual model of a corrected or adjusted anatomical configuration (which can also be referred to herein as a "planned configuration," an "optimized geometry," a "post-operative anatomical configuration," and/or a "target outcome") for the patient. For example, the computing system can, using the analysis procedures described previously, determine a "corrected" or "optimized" anatomical configuration for the particular patient that represents an ideal surgical outcome for the particular patient. This can be done, for example, by analyzing a plurality of reference patient data sets to identify post-operative anatomical configurations for similar patients who had a favorable post-operative outcome, as previously described in detail with respect to FIGS. 1A-3 (e.g., based on similarity of the reference patient data set to the patient data set and/or whether the reference patient had a favorable treatment outcome). This may also include applying one or more mathematical rules defining optimal anatomical outcomes (e.g., positional relationships between anatomic elements) and/or target (e.g., acceptable) post-operative metrics/design criteria (e.g., adjust anatomy so that the post-operative sagittal vertical axis is less than 7 mm, the post-operative Cobb angle less than 10 degrees, the sacroiliac joint fused at the S1 and/or S2 vertebrae, load transfer to sacroiliac joint is reduced by 5%, patient pain score is reduced by at least 10%, etc.). Target post-operative metrics can include, but are not limited to, target coronal parameters, target sagittal parameters, target pelvic incidence angle, target Cobb angle, target shoulder tilt, target iliolumbar angle, target coronal balance, target Cobb angle, target lordosis angle, a target intervertebral space height, and/or a target mobility or range of motion for one or more vertebral bodies and/or joints (e.g., sacroiliac joint) after a fusion procedure. The difference between the native anatomical configuration and the corrected anatomical configuration may be referred to as a "patient-specific correction," a "target correction," an "adjustment," and/or a "patient-specific adjustment."

Once the corrected anatomical configuration is determined, the computing system can generate a two- or three-dimensional visual representation of the patient's anatomy with the corrected anatomical configuration. As with the virtual model created in step 403, the virtual model of the patient's corrected anatomical configuration can include one or more regions of interest, and may include at least part or all of the patient's anatomy within the regions of interest (e.g., any combination of tissue types including, but not limited to, bony structures, cartilage, muscles, ligaments, soft tissue, vascular tissue, nervous tissue, etc.). As a non-limiting example, the virtual model can include a visual representation of the patient's spinal cord region in a corrected anatomical configuration, including at least part or all of the sacrum, lumbar region, thoracic region, and/or cervical region. In some embodiments, the virtual model includes soft tissue, cartilage, and other non-bony structures. In other embodiments, the virtual model only includes the patient's bony structures. An example of a virtual model of the native sacroiliac anatomical configuration is described below with respect to FIGS. 6A and 6B.

The method 400 can continue in step 406 by generating (e.g., automatically generating) a surgical plan for achieving the corrected anatomical configuration shown by the virtual model. The surgical plan can include pre-operative plans, operative plans, post-operative plans, and/or specific spine metrics associated with the optimal surgical outcome. For example, the surgical plans can include a specific surgical procedure for achieving the corrected anatomical configuration. In the context of spinal surgery, the surgical plan may include a specific fusion surgery (e.g., PLIF, ALIF, TLIF, LLIF, DLIF, XLIF, SIJF, etc.) across a specific range of vertebral levels (e.g., L1-L4, L1-5, L3-T12, S1-S5, etc.). Of course, other surgical procedures may be identified for achieving the corrected anatomical configuration, such as non-fusion surgical approaches and orthopedic procedures for other areas of the patient. The surgical plan may also include one or more expected spine metrics (e.g., lumbar lordosis, Cobb angles, pain data, coronal parameters, sagittal parameters, and/or pelvic parameters) corresponding to the expected post-operative patient anatomy. The surgical plan can be generated by a computing system that is the same as or different than the computing system that created the virtual model of the corrected anatomical configuration. In some embodiments, the surgical plan can also be based on one or more reference patient data sets as previously described with respect to FIGS. 1A-3. In some embodiments, the surgical plan can also be based at least in part on surgeon-specific preferences and/or outcomes associated with a specific surgeon performing the surgery. In some embodiments, the surgical plan can also be based at least in part on models or simulations (e.g., biomechanical simulations) of the patient's anatomy, such as simulations of spinal load transfer via one or both of the sacroiliac joints to the coxal bones of the patient. In some embodiments, more than one surgical plan is generated in step 406 to provide a surgeon with multiple options.

After the virtual model of the corrected anatomical configuration is created in step 404 and the surgical plan is generated in step 406, the method 400 can continue in step 408 by transmitting the virtual model of the corrected anatomical configuration and the surgical plan for surgeon review. In some embodiments, the virtual model and the surgical plan are transmitted as a surgical plan report. In some embodiments, the same computing system used in steps 402-406 can also transmit the virtual model and surgical plan to a computing device for surgeon review (e.g., the client computing device 102 described in FIG. 1A or the computing device 502 described below with respect to FIG. 5). This can include directly transmitting the virtual model and/or the surgical plan to the computing device, and/or uploading the virtual model and/or the surgical plan to a cloud or other storage system for subsequent downloading. Although step 408 describes transmitting the surgical plan and the virtual model to the surgeon, one skilled in the art will appreciate from the disclosure herein that images of the virtual model may be included in the surgical plan transmitted to the surgeon, and that the actual model need not be included (e.g., to decrease the file size being transmitted). Additionally, the information transmitted to the surgeon in step 408 may include the virtual model of the patient's native anatomical configuration (or images thereof) in addition to the virtual model of the corrected anatomical configuration. In embodiments in which more than one surgical plan is generated in step 406, the method 400 can include transmitting more than one surgical plan to the surgeon for review and selection.

The surgeon can review the virtual model and/or surgical plan and, in step 410, either approve or reject the surgical plan (and/or, if more than one surgical plan is provided in step 408, select one of the provided surgical plans). If the surgeon does not approve the surgical plan in step 410, the surgeon can optionally provide feedback and/or suggested modifications to the surgical plan (e.g., by adjusting the virtual model or changing one or more aspects about the plan). Accordingly, the method 400 can include receiving (e.g., via the computing system) the surgeon feedback and/or suggested modifications. If surgeon feedback and/or suggested modifications are received in step 412, the method 400 can continue in step 414 by revising (e.g., automatically revising via the computing system 100) the virtual model and/or surgical plan based at least in part on the surgeon feedback and/or suggested modifications received in step 412. In some embodiments, the surgeon does not provide feedback and/or suggested modifications if they reject the surgical plan. In such embodiments, step 412 can be omitted, and the method 400 can continue in step 414 by revising (e.g., automatically revising via the computing system 100) the virtual model and/or the surgical plan by selecting new and/or additional reference patient data sets. The revised virtual model and/or surgical plan can then be transmitted to the surgeon for review. Steps 408, 410, 412, and 414 can be repeated as many times as necessary until the surgeon approves the surgical plan. Although described as the surgeon reviewing, modifying, approving, and/or rejecting the surgical plan, in some embodiments the surgeon can also review, modify, approve, and/or reject the corrected anatomical configuration shown via the virtual model.

Once surgeon approval of the surgical plan is received in step 410, the method 400 can continue in step 416 by designing (e.g., via the same computing system that performed steps 402-414) at least one patient-specific implant based at least partially on the corrected anatomical configuration and/or the surgical plan. For example, each patient-specific implant can be specifically designed such that, when implanted in the particular patient, it directs the patient's anatomy to occupy the corrected anatomical configuration (e.g., transforming the patient's anatomy from the native anatomical configuration to the corrected anatomical configuration). In a non-limiting example, this can include altering the relative positions or alignment of one or more vertebral bodies, fusing one or more vertebral bodies at a specific vertebral level, and/or fusing one or both of a patient's sacroiliac joints. Each patient-specific implant can be designed such that, when implanted, it causes the patient's anatomy to occupy the corrected anatomical configuration for the expected service life of the implant (e.g., 5 years or more, 10 years or more, 20 years or more, 50 years or more, etc.). In some embodiments, each patient-specific implant is designed solely based on the virtual model of the corrected anatomical configuration and/or without reference to pre-operative patient images.

Each patient-specific implant can be any of the implants described herein and/or in any patent references incorporated by reference herein. For example, the patient-specific implant can include one or more of screws (e.g., bone screws, spinal screws, pedicle screws, facet screws), interbody implant devices (e.g., intervertebral implants), cages, plates, rods, discs, fusion devices, spacers, rods, expandable devices, stents, brackets, ties, scaffolds, fixation device, anchors, nuts, bolts, rivets, connectors, tethers, fasteners, joint replacements (e.g., artificial discs), hip implants, or the like. A patient-specific implant design can include data representing one or more of physical properties (e.g., size, shape, volume, material, mass, weight), mechanical properties (e.g., stiffness, strength, modulus, hardness), and/or biological properties (e.g., osteo-integration, cellular adhesion, anti-bacterial properties, anti-viral properties) of the implant. For example, a design for a patient-specific orthopedic implant can include implant shape, size, material, and/or effective stiffness (e.g., lattice density, number of struts, location of struts, etc.). Examples of patient-specific sacroiliac joint implants that can be designed via the method 400 are described previously and with reference to FIGS. 1C-1D, and below and with reference to FIG. 8.

In some embodiments, designing the implant in step 416 can optionally include generating fabrication instructions for manufacturing the implant. For example, the computing system may generate computer-executable fabrication instructions that that, when executed by a manufacturing system, cause the manufacturing system to manufacture the implant. In some embodiments, designing the implant in step 426 includes generating CAD models and/or design parameters that can be used by a manufacturing system to generate computer-executable fabrication instructions, as described below.

In some embodiments, the patient-specific implant is designed in step 416 only after the surgeon has reviewed and approved the virtual model with the corrected anatomical configuration and the surgical plan. Accordingly, in some embodiments, the implant design is neither transmitted to the surgeon with the surgical plan in step 408, nor manufactured before receiving surgeon approval of the surgical plan. Without being bound by theory, waiting to design the patient-specific implant until after the surgeon approves the surgical plan may increase the efficiency of the method 400 and/or reduce the resources necessary to perform the method 400.

The method 400 can continue in step 418 by manufacturing the patient-specific implant. The implant can be manufactured using additive manufacturing techniques, such as 3D printing, stereolithography, digital light processing, fused deposition modeling, selective laser sintering, selective laser melting, electronic beam melting, laminated object manufacturing, powder bed printing, thermoplastic printing, direct material deposition, or inkjet photo resin printing, or like technologies, or combination thereof. Alternatively, or additionally, the implant can be manufactured using subtractive manufacturing techniques, such as CNC machining, electrical discharge machining (EDM), grinding, laser cutting, water jet machining, manual machining (e.g., milling, lathe/turning), and/or like technologies, and/or combinations thereof. The implant may be manufactured by any suitable manufacturing system (e.g., the manufacturing system 124 shown in FIG. 1A or the manufacturing system 530 described below with respect to FIG. 5). In some embodiments, the implant is manufactured by the manufacturing system executing the computer-readable fabrication instructions generated by the computing system in step 416.

In some embodiments, manufacturing the patient-specific implant at step 418 can be performed at a location remote from the computing system used to perform one or more of steps 402-416. In such embodiments, step 416 can include receiving fabrication instructions or manufacturing data from the remote computing systems over a wireless network. In other embodiments, step 416 includes receiving, at a manufacturing systems, other manufacturing data associated with the patient-specific implant, such as CAD models and/or design parameters. Representative design parameters can include, for example, implant shapes, dimensions, materials, material properties, density, porosity, lattice structure, surface finishes, and the like. The manufacturing system can then manufacture the patient-specific implant based on the CAD models and/or design parameters. In embodiments in which the manufacturing system receives CAD models and/or design parameters, the manufacturing system may generate computer-executable fabrication instructions based on the CAD models and/or design parameters. The computer executable fabrication instructions can then control the manufacturing system to manufacture the patient-specific implant.

Once the implant is manufactured in step 418, the method 400 can continue in step 420 by implanting the patient-specific implant into the patient. The surgical procedure can be performed manually, by a robotic surgical platform (e.g., a surgical robot), and/or a combination thereof. In embodiments in which the surgical procedure is performed at least in part by a robotic surgical platform, the surgical plan can include computer-readable control instructions configured to cause the surgical robot to perform at least part or all of the patient-specific surgical procedure. Additional details regarding a robotic surgical platform are described below with respect to FIG. 5.

In some embodiments, the method 400 can further include performing or more models or simulations, such as biomechanical simulations, based on the native virtual model of step 403 and/or the corrected virtual model of step 404. The biomechanical simulations can be used to determine, analyze, and/or predict the effect of one or more forces or loads (e.g., compressive loads, shear loads, etc.) applied to the patient's anatomy before and/or after a surgical procedure, such as a surgical procedure included as part of the surgical plan of step 406. In some embodiments, the biomechanical simulations can include predicting forces applied to the patient's anatomy from one or more muscles and/or ligaments (e.g., simulated muscles and/or ligaments). In some embodiments, the biomechanical simulations can include simulating spinal load transfer between a first anatomical feature and a second anatomical feature, such as between two vertebral bodies, between a sacrum and an ilium, and/or between a portion of a patient's spine and a sacroiliac joint. In some embodiments, the biomechanical simulations can include simulating loads or forces based on a range of motion of an anatomical feature of the patient (e.g., a range of motion on the spine), and determining whether the simulated load is acceptable, as described previously. The biomechanical simulations can be performed using computational models, multibody models, finite element models, and/or any other suitable process or techniques known to those of skill in the art.

The method 400 can be implemented and performed in various ways. In some embodiments, steps 402-416 can be performed by a computing system (e.g., the computing system 506 described below with respect to FIG. 5) associated with a first entity, step 418 can be performed by a manufacturing system associated with a second entity, and step 420 can be performed by a surgical provider, surgeon, and/or robotic surgical platform associated with a third entity. Any of the foregoing steps may also be implemented as computer-readable instructions stored in memory and executable by one or more processors of the associated computing system(s).

Figure 4B:
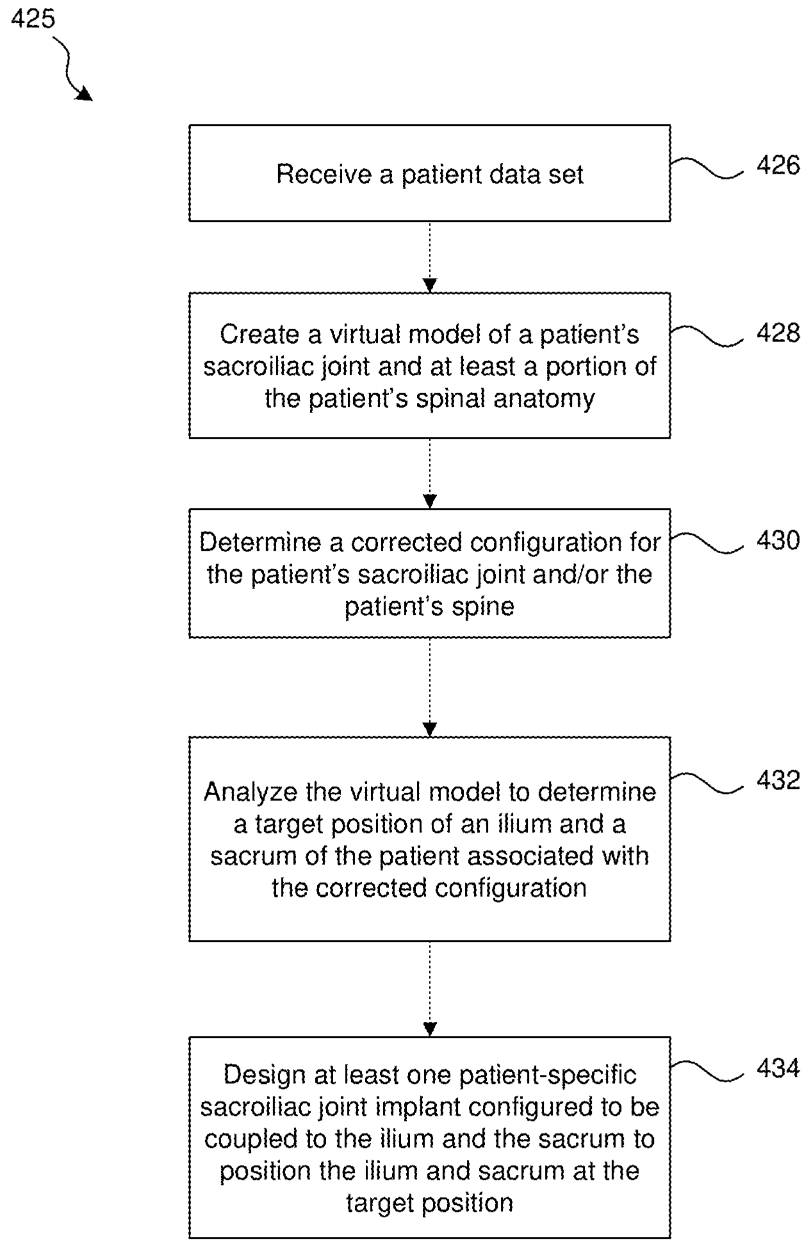
FIG. 4B is a flow diagram illustrating a method for providing patient-specific medical care for a patient's sacroiliac joint, in accordance with embodiments of the present technology.

FIG. 4B is a flow diagram illustrating a method 425 for providing patient-specific medical care for a patient's sacroiliac joint, in accordance with embodiments of the present technology. The method 425 can begin in step 426 by receiving a patient data set for a particular patient in need of medical treatment. Step 426 can by generally similar to or the same as step 402 of the method 400 of FIG. 4A. In step 426, the patient data set received has patient data associated with the patient's SI joint. Representative patient data may include, for example, X-rays or other images of the patient's sacrum and pelvis from a plurality of views (e.g., anterior, posterior, lateral) and under a variety of conditions (sitting, standing, load-bearing, non-load-bearing). Representative patient data may also include (i) pain scores specific to patient pain at or associated with the patient's sacrum, pelvis, or SI joint, (ii) movement or kinetic data associated with mobility of the patient's SI joint. (iii) load-bearing data indicative of loads at the sacrum, iliac, or SI joint under a variety of conditions (standing, sitting, laying, etc.), and/or other suitable patient data.

The method 425 can continue in step 428 by creating a virtual model of a patient's sacroiliac joint and at least a portion of the patient's spine/spinal anatomy. Step 428 can be generally similar to or the same as step 402 of the method 400 of FIG. 4A. For example, in step 426, the virtual model can be generated based on the X-rays or other image data included in the patient data set received in step 426. The virtual model can be a two- or three-dimensional visual representation of the patient's native anatomy, e.g., the patient's native sacroiliac joint anatomy and the portion of the patient's spinal anatomy.

The method 425 can continue in step 430 by determining a corrected configuration for the patient's sacroiliac joint and/or the patient's spine. Step 430 can be generally similar or the same as step 404 of the method 400. For example, using the analysis procedures described previously, a computing system can determine a "corrected" or "optimized" anatomical configuration for the particular patient that represents an ideal surgical outcome for the particular patient. This can be done, for example, by analyzing a plurality of reference patient data sets to identify post-operative anatomical configurations for similar patients who had a favorable post-operative outcome, as previously described in detail with respect to FIGS. 1A-3 (e.g., based on a similarity of the reference patient data set to the patient data set and/or whether the reference patient had a favorable treatment outcome). In some embodiments, step 430 can include creating a virtual model of the corrected or adjusted anatomical configuration for the patient based on the determined corrected configuration.

In some embodiments, step 430 can include identifying one or more regions of the patient's spine for adjustment, and adjusting one or more anatomic elements of the native virtual model of step 428 to produce the corrected configuration for the patient's spine. This is described in greater detail below and with reference to FIGS. 6A-7B

The method 425 can continue at step 432 by analyzing the virtual model (e.g., the native virtual model of step 428 and/or the corrected virtual model of step 430) to determine a target position of an ilium and a sacrum of the patient associated with the corrected configuration determined in step 430. For example, the target position of the ilium and the sacrum can be the position of the ilium and sacrum that naturally occurs following the adjustment to the patient's pre-operative native anatomy performed virtually in step 432. For example, if in step 430 a corrected configuration is determined for the patient's SI joint, the target position of the ilium and the sacrum can be the position that causes the SI joint to assume the corrected configuration. Likewise, if in step 430 a corrected configuration is determined for the patient's lumbar region, the target position of the ilium and the sacrum can be the position the ilium and sacrum naturally occupy when the patient's lumbar region is positioned in the corrected configuration. In other embodiments, the target position of the ilium and the sacrum can be different than the position of the ilium and sacrum that naturally occurs following the adjustment to the patient's pre-operative native anatomy performed virtually in the step 432. For example, in some embodiments an additional positional adjustment for the ilium and/or sacrum may provide additional symptomatic relief for the patient, such as by reducing movement at the SI joint, increasing spacing at the SI joint, improving mobility at the SI joint, or the like. The target position can be part of a surgical plan for achieving the corrected anatomical configuration of step 430. The surgical plan can include pre-operative plans, operative plans, post-operative plans, and/or specific spine metrics associated with the optimal surgical outcome. For example, the surgical plans can include a specific surgical procedure for achieving the corrected anatomical configuration, such as a sacroiliac joint fusion procedure. The target position can include one or more sacral vertebral levels (e.g., one or more of S1-S5) where an implant can couple (e.g., join, fuse, etc.) the patient's sacrum and ilium. The surgical plan may also include one or more expected spine metrics (e.g., lumbar lordosis, Cobb angles, pain data, coronal parameters, sagittal parameters, and/or pelvic parameters) corresponding to the expected post-operative patient anatomy. In some embodiments, the surgical plan can also be based on one or more reference patient data sets as previously described with respect to FIGS. 1A-3.

In some embodiments, step 432 can further include moving or transitioning the virtual model of the patient's spinal anatomy to the corrected configuration, determining the target position of the ilium and the sacrum for achieving the corrected configuration for the patient's spine, and identifying an implant location along the patient's sacroiliac joint based on the target position. In some embodiments, step 432 can further include predicting post-operative compressive and/or shear forces in at least one of the patient's sacroiliac joints. The predicted post-operative compressive and/or shear forces can be based at least partially on the patient data sets and/or a simulation (e.g., a biomechanical simulation) performed based on the patient's virtual anatomy. In some embodiments, step 432 can further include modeling one or more muscles and/or ligaments, and predicting one or more forces applied to the at least one sacroiliac joint based on the modeled muscles and/or ligaments.

The method 425 can continue at step 434 by designing at least one patient-specific sacroiliac joint implant configured to be coupled to the ilium and the sacrum when the ilium and the sacrum occupy the target position determined in step 432. Step 434 can be generally similar to or the same as step 416 of the method 400 of FIG. 4A. For example, the patient-specific sacroiliac joint implant can be specifically designed such that, when it is implanted in the particular patient at the target position, it directs the patient's anatomy to occupy the corrected anatomical configuration (e.g., transforming the patient's anatomy from the native anatomical configuration to the corrected anatomical configuration) and/or directs the patient's sacrum and ilium to assume the target position. In a non-limiting example, this can include fusing one or both of the patient's sacroiliac joints (e.g., to hold the patient's sacrum and/or ilium at the target position) and/or altering the relative positions or alignment of one or more vertebral bodies (e.g., to direct the patient's anatomy into the corrected configuration). In some embodiments, the patient-specific sacroiliac joint implant is designed solely based on the virtual model of the corrected anatomical configuration (step 430) and/or without reference to pre-operative patient images. The patient-specific sacroiliac joint implant can have topology that matches a topology of the patient's sacroiliac joint and can be any of the implants described herein or in any patent references incorporated by reference herein. For example, the patient-specific sacroiliac joint implant can include one or more screws (e.g., bone screws, spinal screws, pedicle screws, facet screws), inter-body implant devices (e.g., intervertebral implants), cages, plates, rods, discs, fusion devices, spacers, rods, expandable devices, stents, brackets, ties, scaffolds, fixation device, anchors, nuts, bolts, rivets, connectors, tethers, fasteners, joint replacements (e.g., artificial discs), hip implants, and/or the like.

In some embodiments, the patient-specific sacroiliac implant can be designed based at least in part on predicted post-operative compressive or shear forces at the SI joint, determined at step 432. For example, the implant can be designed to withstand compressive or shear forces up to at least 20% greater than, at least 50% greater than, at 100% greater than, or at least 200% greater than the predicted post-operative compressive or shear forces to reduce the likelihood of device failure. Design features that can impact shear forces of the implant include, for example, implant dimensions (e.g., length vs. cross-sectional area), implant material, implant rigidity, implant anchoring, etc. In some embodiments, multiple SI implants are designed for implantation. In such embodiments, the multiple SI implants can be designed such that compressive or shear forces are distributed equally, or about equally, across each implant.

In some embodiments, the method 425 can further include performing one or more biomechanical simulations on the patient's anatomy. In at least some embodiments, for example, the method 425 can include performing a biomechanical simulation of spinal load transfer via the sacroiliac joint(s) to one or more coxal bones of the patient. In at least some embodiments, for example, the one or more biomechanical simulations can include performing pre-operative and/or post-operative simulations to predict patient outcomes based on simulated sacroiliac joint adjustments. The predicted patient outcomes can be based at least partially on the patient data sets. The biomechanical simulation can be performed using the native virtual model of step 428 and/or the corrected virtual model of step 430.

In some embodiments, the method 425 can further include receiving pain data corresponding to the particular patient. The pain data can be used to determine one or more adjustments to the native virtual model of step 428. The one or more adjustments can be used to determine a pain reduction score and/or a change (e.g., an expected or predicted change) in pain score. The pain reduction score and/or the change in pain score can be based at least partially on reference patient data (e.g., reference patient pain data), and can be determined prior to designing and/or manufacturing the at least one patient-specific sacroiliac joint implant (step 434).

Figure 4C:
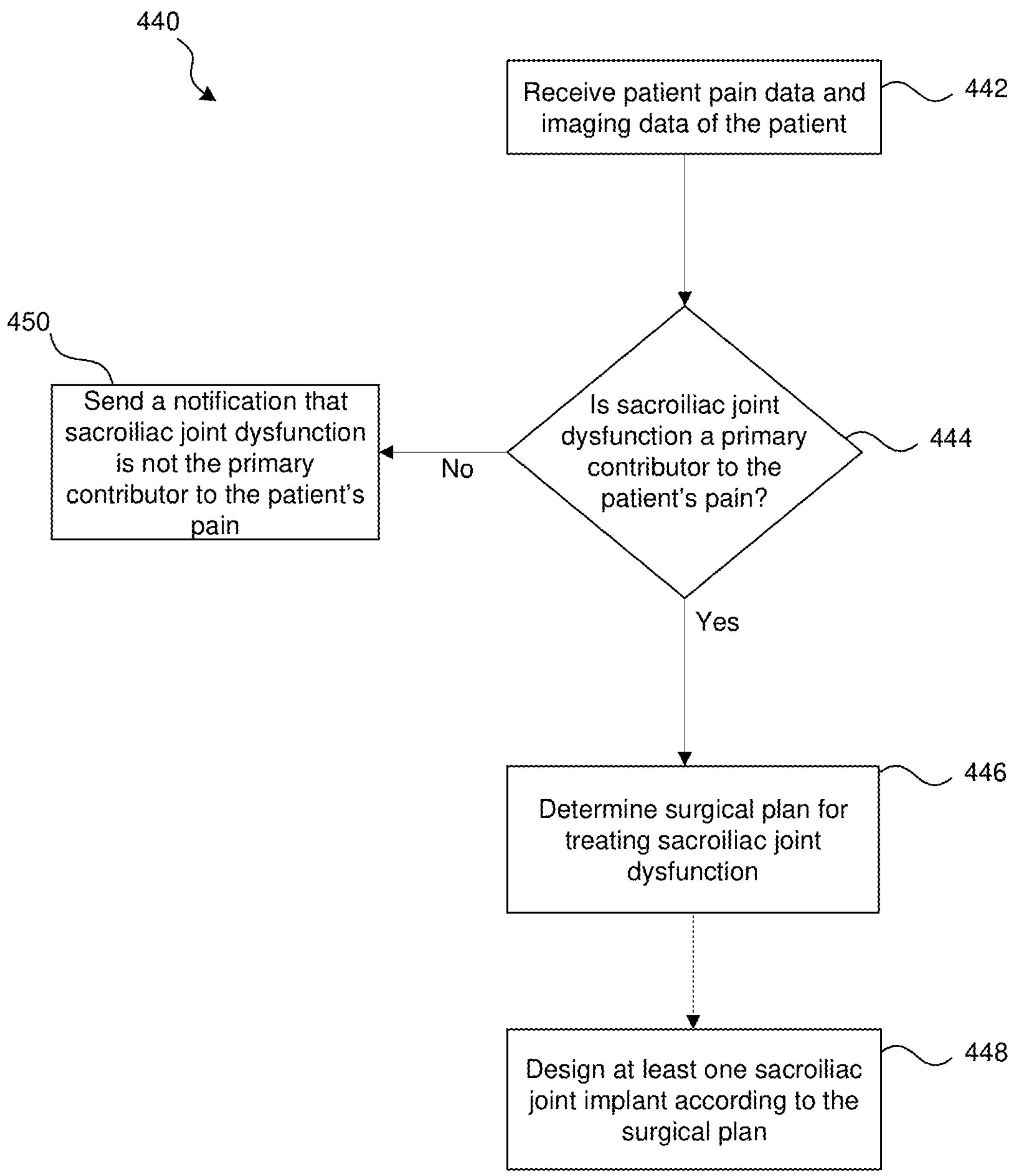
FIG. 4C is a flow diagram illustrating a method for providing patient-specific medical care for a patient's sacroiliac joint based on patient pain data, in accordance with embodiments of the present technology.

FIG. 4C is a flow diagram illustrating a method 440 for providing patient-specific medical care for a patient's sacroiliac joint based on patient pain data, in accordance with embodiments of the present technology. The method 440 can begin in step 442 by receiving pain data and imaging data for a particular patient in need of medical treatment. Step 442 can by generally similar to or the same as step 402 of the method 400 of FIG. 4A.

The method 440 can continue in step 444 by determining whether sacroiliac joint dysfunction is a primary contributor to the patient's pain. In some embodiments, step 444 can include comparing the patient pain data (e.g., step 442) to reference sacroiliac joint dysfunction data to determine whether sacroiliac joint dysfunction is the primary contributor to the patient's pain. The reference sacroiliac joint dysfunction data can include reference patient pain data, and sacroiliac joint dysfunction can correspond to one or more similarities between the patient pain data and the reference patient pain data. For example, if the patient has pain data that is generally similar to or the same as reference patient pain data for a reference patient with known sacroiliac joint dysfunction, then it can be determined that the sacroiliac joint dysfunction is the primary contributor to the patient's pain. In some embodiments, step 444 can include performing one or more tests on the patient to determine whether sacroiliac joint dysfunction is the primary contributor. The one or more tests can include, but are not limited to, a pain pelvic gapping test, a pelvic compression test, a thigh thrusting test, a flexion abduction external rotation test, and/or a Gaenslen test.

If, at step 444, sacroiliac joint dysfunction is determined to be the primary contributor, the method 440 can continue in step 446 by determining a surgical plan for addressing the SI joint dysfunction. This may include, for example, determining an optimal target post-operative pelvic anatomy for the patient, as described above with reference to step 404 of the method 400 (FIG. 4A) and steps 430 and 432 of the method 425 (FIG. 4B). In some embodiments, this may include determining one or more adjustments to a relative positioning of the patient's sacrum and ilium. Additionally or alternatively, step 446 may include determining an appropriate surgical procedure (e.g., SI joint fusion) to address the SI joint dysfunction.

The method 440 can continue in step 448 by designing at least one sacroiliac joint implant according to the surgical plan. In some embodiments, this includes designing one or more SI implants that, when implanted, cause the patient's pelvis to occupy the target post-operative anatomy determined in step 446. Step 434 can be generally similar to or the same as step 416 of the method 400 of FIG. 4A, and/or step 434 of the method 425 of FIG. 4B. For example, the sacroiliac joint implant can be specifically designed such that, when it is implanted in the particular patient at the determined position, it directs the patient's anatomy to occupy the corrected anatomical configuration (e.g., transforming the patient's anatomy from a native anatomical configuration to a corrected anatomical configuration) and can at least partially reduce the patient's pain. If micromovement of the sacral-iliac joint is determined to be the source of the pain, an alternative implantation can be provided to fuse the sacrum to the ilium in the corrected configuration.

If, at step 444, sacroiliac joint dysfunction is determined to not be the primary contributor, the method 440 can continue in step 450 by sending or providing a notification (e.g., to a user, a physician, etc.) that sacroiliac joint dysfunction is not the primary contributor to the patient's pain. In some embodiments, step 450 can further include identifying a treatment plan to reduce patient pain based on repositioning the patient's spine using one or more implanted devices, such as any of the devices described and/or incorporated by reference herein.

The methods 425, 440 can be implemented and performed in various ways. In some embodiments, steps can be performed by a computing system (e.g., the computing system 506 described below with respect to FIG. 5) associated with a first entity. Any of the foregoing steps may also be implemented as computer-readable instructions stored in memory and executable by one or more processors of the associated computing system(s).

Figure 5:
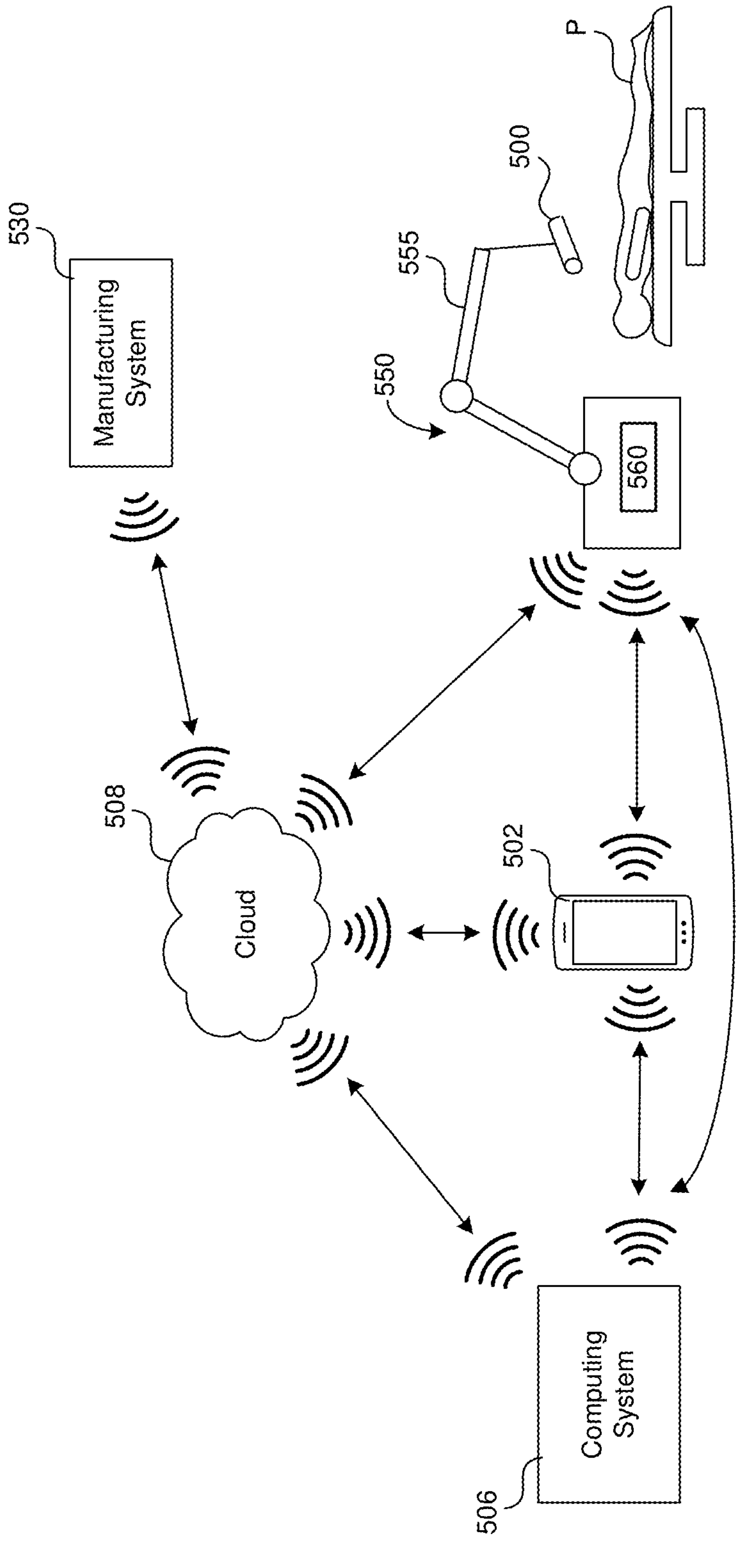
FIG. 5 is a partially schematic illustration of an operative setup and associated computing systems for providing patient-specific medical care, in accordance with embodiments of the present technology.

FIG. 5 is a schematic illustration of an operative setup including select systems and devices that can be used to provide patient-specific medical care, such as for performing one or more steps of the methods 400, 425, and/or 440 described with respect to FIGS. 4A-4C, respectively, in accordance with embodiments of the present technology. As shown, the operative setup includes a computing device 502, a computing system 506, a cloud 508, a manufacturing system 530, and a robotic surgical platform 550. The computing device 502 can be a user device, such as a smart phone, mobile device, laptop, desktop, personal computer, tablet, phablet, or other such devices known in the art. In operation, a user (e.g., a surgeon) can collect, retrieve, review, modify, or otherwise interact with a patient data set using the computing device 502. The computing system 506 can include any suitable computing system configured to store one or more software modules for identifying reference patient data sets, determining patient-specific surgical plans, generating virtual models of patient anatomy, designing patient-specific implants, or the like. The one or more software modules can include algorithms, machine-learning models, artificial intelligence architectures, or the like for performing select operations. The cloud 508 can be any suitable network and/or storage system, and may include any combination of hardware and/or virtual computing resources. The manufacturing system 530 can be any suitable manufacturing system for producing patient-specific implants, including any of those previously described herein. The robotic surgical platform 550 (referred to herein as "the platform 550") can be configured to perform or otherwise assist with one or more aspects of a surgical procedure.

In a representative operation, the computing device 502, the computing system 506, the cloud 508, the manufacturing system 530, and the platform 550 can be used to provide patient-specific medical care, such as to perform one or more steps of the methods 400,425, and/or 440 described with respect to FIGS. 4A-4C, respectively. For example, the computing system 506 can receive a patient data set from the computing device 502 (e.g., step 402 of the method 400). In some embodiments, the computing device 502 can directly transmit the patient data set to the computing system 506. In other embodiments, the computing device 502 can upload the patient data set into the cloud 508, and the computing system 506 can download or otherwise access the patient data set from the cloud. Once the computing system 506 receives the patient data set, the computing system 506 can create a virtual model of the patient's native anatomical configuration (e.g., step 403 of the method 400), create a virtual model of the corrected anatomical configuration (e.g., step 404 of the method 400), and/or generate a surgical plan for achieving the corrected anatomical configuration (e.g., step 406 of the method 400). The computing system can perform the foregoing operations via the one or more software modules, which in some embodiments include machine learning models or other artificial intelligence architectures. Once the virtual models and the surgical plan are created, the computing system 506 can transmit the virtual models and the surgical plan to the surgeon for review (e.g., step 408 of the method 400). This can include, for example, directly transmitting the virtual models and the surgical plan to the computing device 502 for surgeon review. In other embodiments, this can include uploading the virtual models and the surgical plan to the cloud 508. A surgeon can then download or otherwise access the virtual models and the surgical plan from the cloud 508 using the computing device 502.

The surgeon can use the computing device 502 to review the virtual models and the surgical plan. The surgeon can also approve or reject the surgical plan and provide any feedback regarding the surgical plan using the computing device 502. The surgeon's approval, rejection, and/or feedback regarding the surgical plan can be transmitted to, and received by, the computing system 506 (e.g., steps 410 and 412 of the method 400). The computing system 506 can than revise the virtual model and/or the surgical plan (e.g., step 414 of the method 400). The computing system 506 can transmit the revised virtual model and surgical plan to the surgeon for review (e.g., by uploading it to the cloud 508 or directly transmitting it to the computing device 502).

The computing system 506 can also design the patient-specific implant based on the corrected anatomical configuration and the surgical plan (e.g., step 416 of the method 400) using, the one or more software modules. In some embodiments, software modules rely on one or more algorithms, machine learning models, or other artificial intelligence architectures to design the implant. Once the computing system 506 designs the patient-specific implant, the computing system 506 can upload the design and/or manufacturing instructions to the cloud 508. The computing system 506 may also create fabrication instructions (e.g., computer-readable fabrication instructions) for manufacturing the patient-specific implant. In such embodiments, the computing system 506 can upload the fabrication instructions to the cloud 508.

The manufacturing system 530 can download or otherwise access the design and/or fabrication instructions for the patient-specific implant from the cloud 508. The manufacturing system can then manufacture the patient-specific implant (e.g., step 418 in the method 400) using additive manufacturing techniques, subtractive manufacturing techniques, and/or other suitable manufacturing techniques.

The robotic surgical platform 550 can perform or otherwise assist with one or more aspects of the surgical procedure (e.g., step 420 of the method 400). For example, the platform 550 can prepare tissue for an incision, make an incision, make a resection, remove tissue, manipulate tissue, perform a corrective maneuver, deliver the implant to a target site, deploy the implant at the target site, adjust the implant at the target site, manipulate the implant once it is implanted, secure the implant at the target site, explant the implant, suture tissue, etc. The platform 550 can therefore include one or more arms 555 and end effectors for holding various surgical tools (e.g., graspers, clips, needles, needle drivers, irrigation tools, suction tools, staplers, screwdriver assemblies, etc.), imaging instruments (e.g., cameras, sensors, etc.), and/or medical devices (e.g., the implant 500) and that enable the platform 550 to perform the one or more aspects of the surgical plan. Although shown as having one arm 555, one skilled in the art will appreciate that the platform 550 can have a plurality of arms (e.g., two, three, four, or more) and any number of joints, linkages, motors, and degrees of freedom. In some embodiments, the platform 550 may have a first arm dedicated to holding one or more imaging instruments, while the remainder of the arms hold various surgical tools. In some embodiments, the tools can be releasably secured to the arms such that they can be selectively interchanged before, during, and/or after an operative procedure. The arms can be moveable through a variety of ranges of motion (e.g., degrees of freedom) to provide adequate dexterity for performing various aspects of the operative procedure.

The platform 550 can include a control module 560 for controlling operation of the arm(s) 555. In some embodiments, the control module 560 includes a user input device (not shown) for controlling operation of the arm(s) 555. The user input device can be a joystick, a mouse, a keyboard, a touchscreen, an infrared sensor, a touchpad, a wearable input device, a camera- or image-based input device, a microphone, or other user input devices. A user (e.g., a surgeon) can interact with the user input device to control movement of the arm(s) 555.

In some embodiments, the control module 560 includes one or more processors for executing machine-readable operative instructions that, when executed, automatically control operation of the arm 555 to perform one or more aspects of the surgical procedure. In some embodiments, the control module 560 may receive the machine-readable operative instructions (e.g., from the cloud 508) specifying one or more steps of the surgical procedure that, when executed by the control module 560, cause the platform 550 to perform the one or more steps of the surgical procedure. For example, the machine-readable operative instructions may direct the platform 550 to prepare tissue for an incision, make an incision, make a resection, remove tissue, manipulate tissue, perform a corrective maneuver, deliver the implant 500 to a target site, deploy the implant 500 at the target site, adjust a configuration of the implant 500 at the target site, manipulate the implant 500 once it is implanted, secure the implant 500 at the target site, explant the implant 500, suture tissue, and the like. The operative instructions may therefore include particular instructions for articulating the arm 555 to perform or otherwise aid in the delivery of the patient-specific implant.

In some embodiments, the platform 550 can generate (e.g., as opposed to simply receiving) the machine-readable operative instructions based on the surgical plan. For example, the surgical plan can include information about the delivery path, tools, and implantation site. The platform 550 can analyze the surgical plan and develop executable operative instructions for performing the patient-specific procedure based on the capabilities (e.g., configuration and number of robotic arms, functionality of and effectors, guidance systems, visualization systems, etc.) of the robotic system. This enables the operative setup shown in FIG. 5 to be compatible with a wide range of different types of robotic surgery systems.

The platform 550 can include one or more communication devices (e.g., components having VLC, WiMAX, LTE, WLAN, IR communication, PSTN, Radio waves, Bluetooth, and/or Wi-Fi operability) for establishing a connection with the cloud 508 and/or the computing device 502 for accessing and/or downloading the surgical plan and/or the machine-readable operative instructions. For example, the cloud 508 can receive a request for a particular surgical plan from the platform 550 and send the plan to the platform 550. Once identified, the cloud 508 can transmit the surgical plan directly to the platform 550 for execution. In some embodiments, the cloud 508 can transmit the surgical plan to one or more intermediate networked devices (e.g., the computing device 502) rather than transmitting the surgical plan directly to the platform 550. A user can review the surgical plan using the computing device 502 before transmitting the surgical plan to the platform 550 for execution. Additional details for identifying, storing, downloading, and accessing patient-specific surgical plans are described in U.S. application Ser. No. 16/990,810, filed Aug. 11, 2020, the disclosure of which is incorporated by reference herein in its entirety.

The platform 550 can include additional components not expressly shown in FIG. 5. For example, in various embodiments the platform 550 may include one or more displays (e.g., an LCD display screen, an LED display screen, a projected, holographic, or augmented reality display (e.g., a heads-up display device or a head-mounted device), one or more I/O devices (e.g., a network card, video card, audio card, USB, firewire or other external device, camera, printer, speakers, CD-ROM drive, DVD drive, disk drive, or Blu-Ray device), and/or a memory (e.g., random access memory (RAM), various caches, CPU registers, read-only memory (ROM), and writable non-volatile memory, such as flash memory, hard drives, floppy disks, CDs, DVDs, magnetic storage devices, tape drives, device buffers, and so forth). In some embodiments, the foregoing components can be generally similar to the like components described in detail with respect to computing device 200 in FIG. 2.

Without being bound by theory, using a robotic surgical platform to perform various aspects of the surgical plans described herein is expected to provide several advantages over conventional operative techniques. For example, use of robotic surgical platforms may improve surgical outcomes and/or shorten recovery times by, for example, decreasing incision size, decreasing blood loss, decreasing a length of time of the operative procedure, increasing the accuracy and precision of the surgery (e.g., the placement of the implant at the target location), and the like. The platform 550 can also avoid or reduce user input errors, e.g., by including one or more scanners for obtaining information from instruments (e.g., instruments with retrieval features), tools, the patient specific implant 500 (e.g., after the implant 500 has been gripped by the arm 555), etc. The platform 550 can confirm use of proper instruments prior and during the surgical procedure. If the platform 550 identifies an incorrect instrument or tool, an alert can be sent to a user that another instrument or tool should be installed. The user can scan the new instrument to confirm that the instrument is appropriate for the surgical plan. In some embodiments, the surgical plan includes instructions for use, a list of instruments, instrument specifications, replacement instruments, and the like. The platform 550 can perform pre- and post-surgical checking routines based on information from the scanners.

Figure 6A:
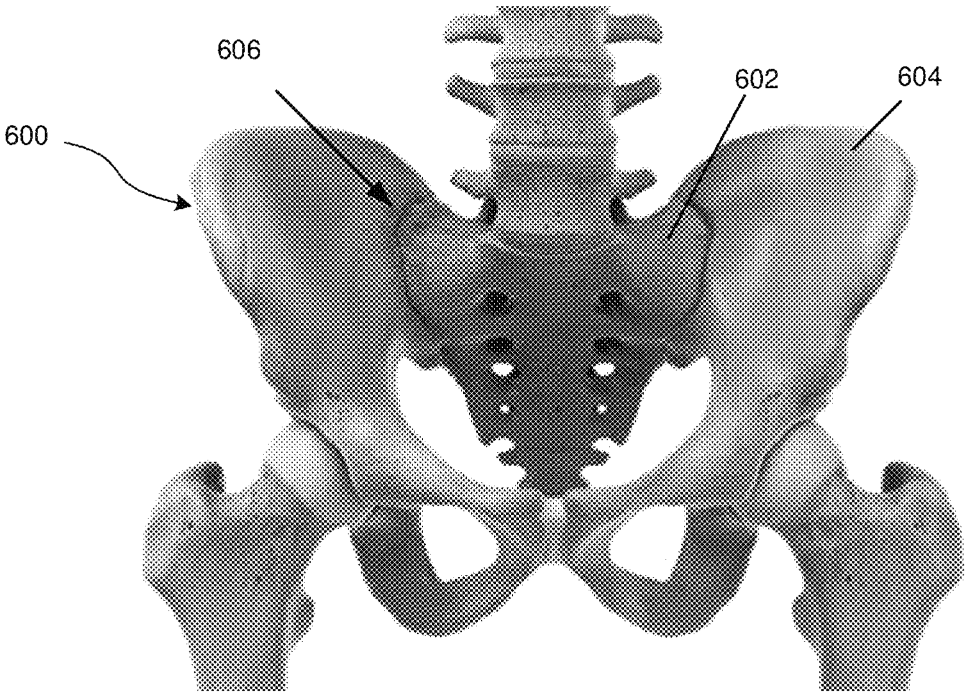
FIGS. 6A and 6B illustrate example virtual models of a patient's spine that may be used and/or generated in connection with the methods described herein, in accordance with embodiments of the present technology.
Figure 6B:
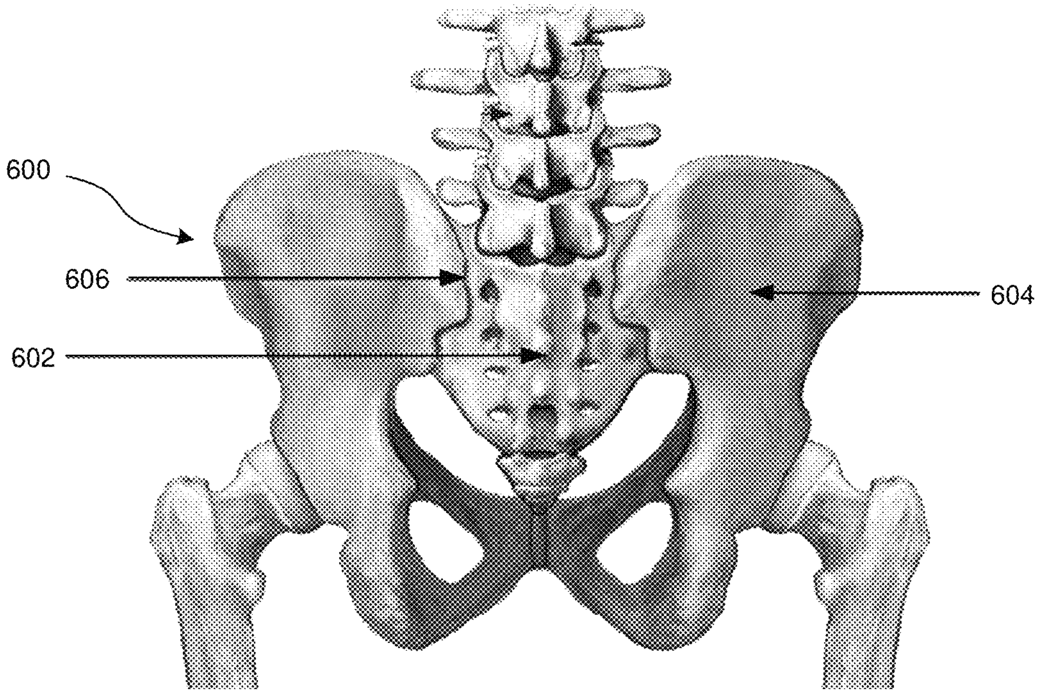

FIGS. 6A and 6B illustrate an example of a virtual model 600 of a patient's native pelvic anatomical configuration (e.g., as created in step 403 of the method 400) in accordance with embodiments of the present technology. In particular, FIG. 6A is an enlarged view of the virtual model 600 of the patient's native anatomy and shows an anterior view of the patient's sacrum 602, ilium 604, and sacroiliac joint 606. FIG. 6B illustrates a posterior view of the virtual model 600 of FIG. 6A. Referring to FIGS. 6A and 6B together, in some embodiments the virtual model can include other regions of the patient's spinal column, including cervical vertebrae, thoracic vertebrae, lumbar vertebrae, etc. The illustrated virtual model 600 only includes bony structures of the patient's anatomy, but in other embodiments may include additional structures, such as cartilage, soft tissue, vascular tissue, nervous tissue, etc. Additionally, in some embodiments the virtual model 600 can include one or more cross sections or cross-sectional views of the patient's anatomy, and/or other suitable views of the patient's anatomy. In some embodiments the virtual model 600 can be interactive such that a user can manipulate the virtual model 600, e.g., to rotate the virtual model between a first view (e.g., the anterior view of FIG. 6A) and a second view (e.g., the posterior view of FIG. 6B).

Figure 7A:
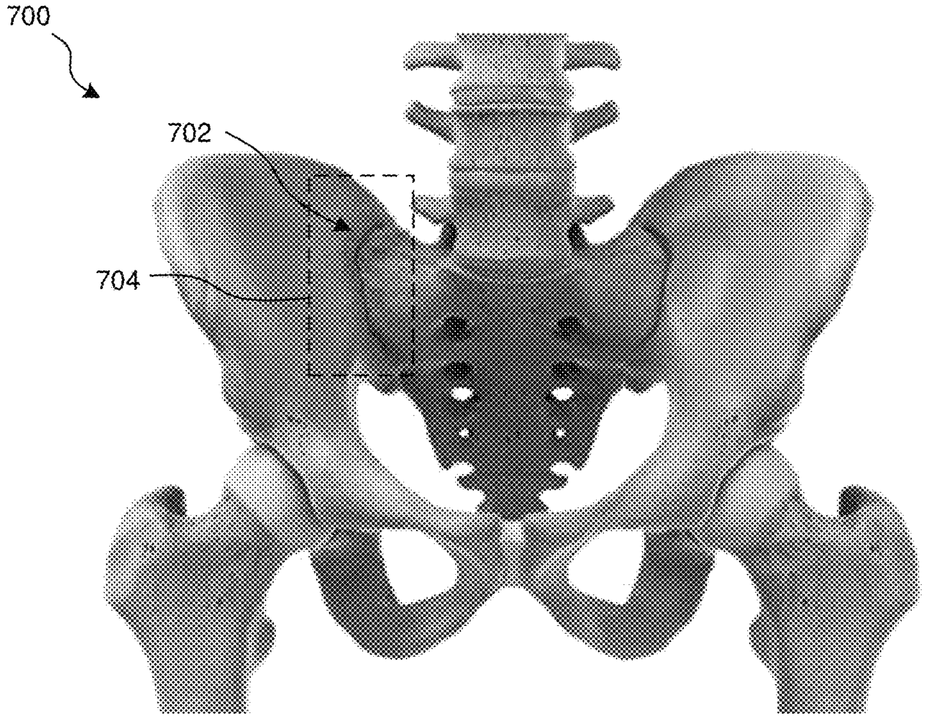
FIG. 7A illustrates an example virtual model of a patient's sacroiliac joint and a portion of the patient's spine in a pre-operative anatomical configuration in accordance with embodiments of the present technology.
Figure 7B:
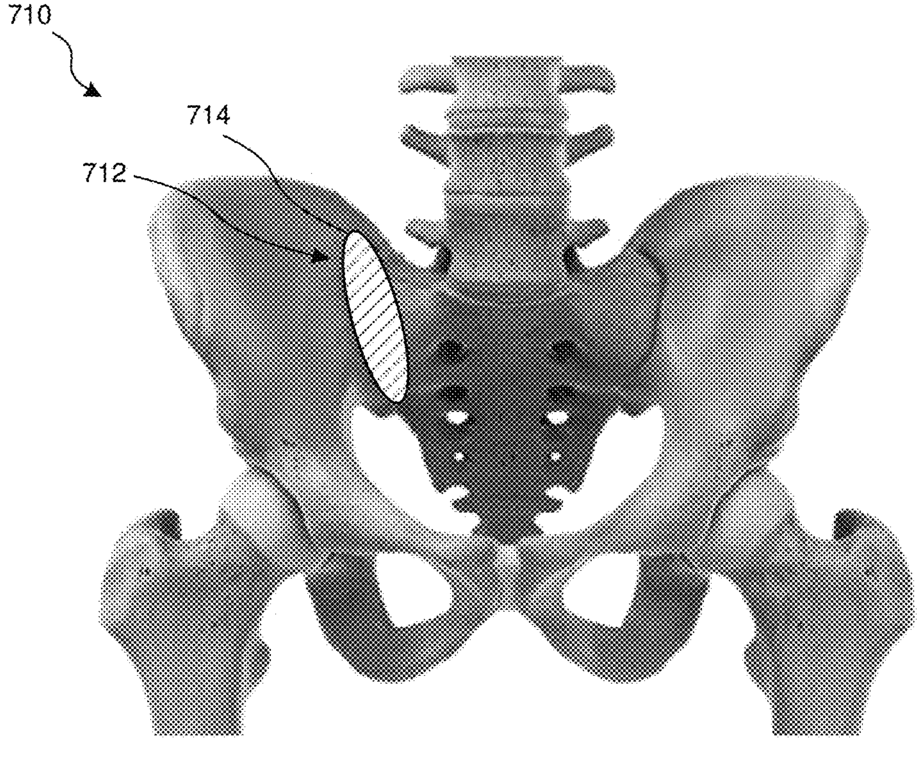
FIG. 7B illustrates the example virtual model of FIG. 7A where the patient's sacroiliac joint is in a corrected configuration.

FIGS. 7A and 7B demonstrate an example of a virtual model of a patient's native anatomical configuration (e.g., as created in step 403 of the method 400) and a virtual model of the patient's corrected anatomical configuration (e.g., as created in step 404 of the method 400) in accordance with embodiments of the present technology. In particular, FIG. 7A is an anterior view of a virtual model 700 showing a native anatomical configuration of a patient, and FIG. 7B is an anterior view of a virtual model 710 showing the corrected anatomical configuration for the same patient.

Referring first to FIG. 7A, the anterior view of the virtual model 700 illustrates the patient has sacroiliac joint dysfunction. This is marked by box 704, which indicates the dysfunctional sacroiliac joint 702. In some embodiments, the virtual model 700 can indicate other dysfunctions or abnormalities related to the patient's sacroiliac joint 702, such as the relative orientation, (mis)alignments, and/or geometries of the sacrum 602, ilium 604, and/or sacroiliac joint 606 (FIGS. 6A and 6B).

Referring next to FIG. 7B, the virtual model 710 illustrates the corrected configuration for the sacroiliac joint 712. This correction is shown in region 714, which illustrates the sacroiliac joint 712 having at least partially corrected or restored function. In some embodiments, the correction shown in the virtual model 710 can include a change in relative orientations and/or alignments of the patient's sacrum 602, ilium 604, and/or sacroiliac joint 606 (FIGS. 6A and 6B). The box 704 and the region 714 are provided in FIGS. 7A and 7B to more clearly demonstrate the correction between the virtual models 700 and 710, and are not necessarily included on the virtual models generated in accordance with the present technology.

Any of the models of FIGS. 6A-7B can be used to perform one or more simulations (e.g., biomechanical simulations) based on the patient's anatomy. In at least some embodiments, for example, the biomechanical simulation(s) can model or simulate one or more forces or loads on a particular patient's anatomy, e.g., to model and/or estimate future anatomical configurations and/or spine metrics of the patient (a) if no surgical intervention occurs, or (b) for a variety of different surgical intervention options. The biomechanical simulation(s) can be used to simulate loading based on a range of motion of a patient's spine before and/or after surgical intervention. In at least some embodiments, for example, the present technology can include performing a biomechanical simulation of spinal load transfer via the sacroiliac joint(s) to the patient's coxal bones over a range of motion of the patient's spine. The simulated loading can be used to predict one or more post-operative forces or loads on the patient's anatomy. In at least some embodiments, for example, the simulated loading can be used to predict a post-operative compressive force and/or a post-operative shear force on at least one of a patient's sacroiliac joints. In some embodiments, the biomechanical simulations can include modeling one or more muscles and/or ligaments operably coupled to a patient's anatomy (e.g., a spine, one or more vertebral bodies, etc.), and predicting one or more forces applied to at least one of a patient's sacroiliac joints based on the modeled muscle(s) and/or ligament(s). The biomechanical simulations can be performed using computational models, multibody models, finite element models, and/or any other suitable process or techniques known to those of skill in the art.

Figure 8:
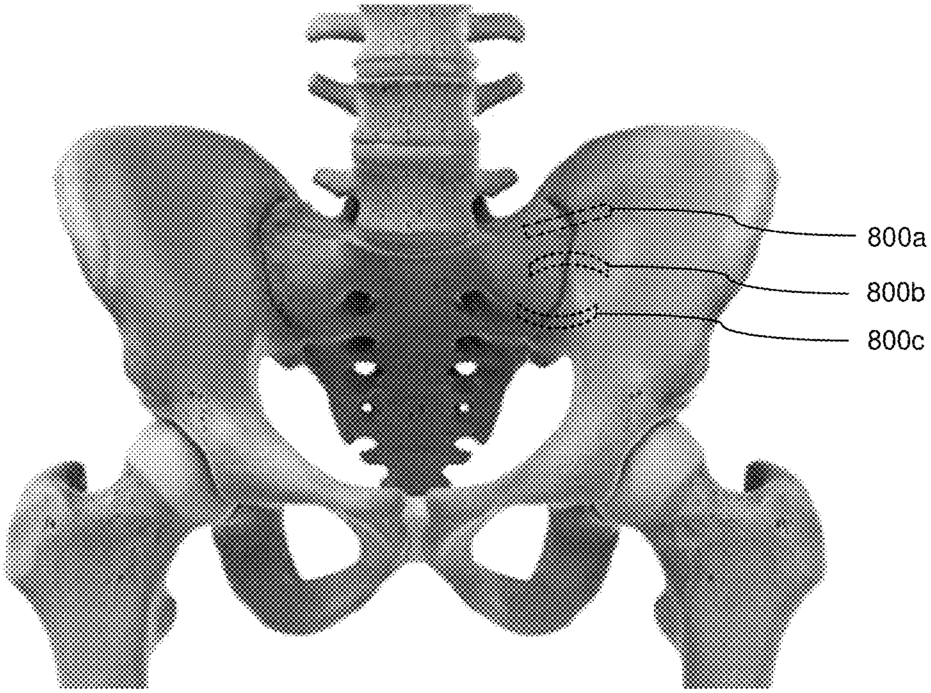
FIG. 8 illustrates a patient's sacroiliac joint after several patient specific sacroiliac joint implants have been implanted therein, in accordance with embodiments of the present technology.

The patient-specific medical procedures described herein can involve implanting more than one patient-specific implant into the patient to achieve the corrected anatomical configuration (e.g., a multi-site procedure). For example, FIG. 8 illustrates a sacroiliac joint having three patient-specific sacroiliac joint implants 800*a-c* (e.g., "the implants 800*a-c*"). More specifically, a first implant 800*a* is implanted dorsally from the S5-L1 disk, a second implant 800*b* is implanted ventrally from the first implant 800*a* and between the S5 vertebra and the S5-L1 disk, and a third implant 800*c* is implanted between the S4 and S5 vertebra. The first, second, and third implants 800*a-c* are patient-specific. For example, the first implant 800*a* is implanted in a first position at a first angle (e.g., relative to the patient's sagittal, coronal, and/or transverse plane), the second implant 800*b* has a first curvature and has been implanted at a second position, and the third implant 800*c* has a second curvature and has been implanted at a third position. Together, the implants 800*a-c* can cause the patient's sacroiliac joint to assume the previously identified corrected anatomical configuration (e.g., transforming the patient's anatomy from its pre-operative diseased configuration to the post-operative optimized configuration). In some embodiments, more or fewer sacroiliac joint implants are used to achieve the corrected anatomical configuration. For example, in some embodiments one, two, four, five, six, seven, eight, or more sacroiliac joint implants are used to achieve the corrected anatomical configuration. In embodiments involving more than one sacroiliac joint implant, the sacroiliac joint implants do not necessarily have the same shape, size, or function. In fact, the multiple sacroiliac joint implants will often have different geometries and topographies to correspond to the target position or region at which they will be implanted. As also shown in FIG. 8, the patient-specific medical procedures described herein can involve treating the patient at multiple target regions. Additional features of patient-specific implants that can be designed and manufactured in accordance with the present technology are described in U.S. patent application Ser. Nos.

16/987,113 and 17/100,396, the disclosures of which are incorporated by reference herein in their entireties.

In addition to designing patient-specific medical care based off reference patient data sets, the systems and methods of the present technology may also design patient-specific medical care based off disease progression for a particular patient. In some embodiments, the present technology therefore includes software modules (e.g., machine learning models or other algorithms) that can be used to analyze, predict, and/or model disease progression for a particular patient. The machine learning models can be trained based off a plurality of reference patient data sets that includes, in addition to the patient data described with respect to FIG. 1A, disease progression metrics for each of the reference patients. The progression metrics can include measurements for disease metrics over a period of time. Suitable metrics may include spinopelvic parameters (e.g., lumbar lordosis, pelvic tilt, sagittal vertical axis (SVA), cobb angel, coronal offset, etc.), disability scores, functional ability scores, flexibility scores, VAS pain scores, or the like. The progression of the metrics for each reference patient can be correlated to other patient information for the specific reference patient (e.g., age, sex, height, weight, activity level, diet, etc.).

In some embodiments, the present technology includes a disease progression module that includes an algorithm, machine learning model, or other software analytical tool for predicting disease progression in a particular patient. The disease progression module can be trained based on reference patient data sets that includes patient information (e.g., age, sex, height, weight, activity level, diet) and disease metrics (e.g., diagnosis, spinopelvic parameters such as lumbar lordosis, pelvic tilt, sagittal vertical axis, cobb angel, coronal offset, etc., disability scores, functional ability scores, flexibility scores, VAS pain scores, etc.). The disease metrics can include values over a period of time. For example, the reference patient data may include values of disease metrics on a daily, weekly, monthly, bi-monthly, yearly, or other basis. By measuring the metrics over a period of time, changes in the values of the metrics can be tracked as an estimate of disease progression and correlated to other patient data.

In some embodiments, the disease progression module can therefore estimate the rate of disease progression for a particular patient. The progression may be estimated by providing estimated changes in one or more disease metrics over a period of time (e.g., X % increase in a disease metric per year). The rate can be constant (e.g., 5% increase in pelvic tilt per year) or variable (e.g., 5% increase in pelvic tilt for a first year, 10% increase in pelvic tilt for a second year, etc.). In some embodiments, the estimated rate of progression can be transmitted to a surgeon or other healthcare provider, who can review and update the estimate, if necessary.

As a non-limiting example, a particular patient who is a fifty-five-year-old male may have a SVA value of 6 mm. The disease progression module can analyze patient reference data sets to identify disease progression for individual reference patients have one or more similarities with the particular patient (e.g., individual patients of the reference patients who have an SVA value of about 6 mm and are approximately the same age, weight, height, and/or sex of the patient). Based on this analysis, the disease progression module can predict the rate of disease progression if no surgical intervention occurs (e.g., the patient's VAS pain scores may increase 5%, 10%, or 15% annually if no surgical intervention occurs, the SVA value may continue to increase by 5% annually if no surgical intervention occurs, etc.).

The systems and methods described herein can also generate models/simulations based on the estimated rates of disease progression, thereby modeling different outcomes over a desired period of times. Additionally, the models/simulations can account for any number of additional diseases or condition to predict the patient's overall health, mobility, or the like. These additional diseases or conditions can, in combination with other patient health factors (e.g., height, weight, age, activity level, etc.) be used to generate a patient health score reflecting the overall health of the patient. The patient health score can be displayed for surgeon review and/or incorporated into the estimation of disease progression. Accordingly, the present technology can generate one or more virtual simulations of the predicted disease progression to demonstrate how the patient's anatomy is predicted to change over time. Physician input can be used to generate or modify the virtual simulation(s). The present technology can generate one or more post-treatment virtual simulations based on the received physician input for review by the healthcare provider, patient, etc.

In some embodiments, the present technology can also predict, model, and/or simulate disease progression based on one or more potential surgical interventions. For example, the disease progression module may simulate what a patient's anatomy may look like 1, 2, 5, or 10 years post-surgery for several surgical intervention options. The simulations may also incorporate non-surgical factors, such as patient age, height, weight, sex, activity level, other health conditions, or the like, as previously described. Based on these simulations, the system and/or a surgeon can select which surgical intervention is best suited for long-term efficacy. These simulations can also be used to determine patient-specific corrections that compensate for the projected diseases progression.

Accordingly, in some embodiments, multiple disease progression models (e.g., two, three, four, five, six, or more) are simulated to provide disease progression data for several different surgical intervention options or other scenarios. For example, the disease progression module can generate models that predict post-surgical disease progression for each of three different surgical interventions. A surgeon or other healthcare provider can review the disease progression models and, based on the review, select which of the three surgical intervention options is likely to provide the patient with the best long-term outcome. Of course, selecting the optimal intervention can also be fully or semi-automated, as described herein.

Based off of the modeled disease progression, the systems and methods described herein can also (i) identify the optimal time for surgical intervention, and/or (ii) identify the optimal type of surgical procedure for the patient. In some embodiments, the present technology therefore includes an intervention timing module that includes an algorithm, machine learning model, or other software analytical tool for determining the optimal time for surgical intervention in a particular patient. This can be done, for example, by analyzing patient reference data that includes (i) pre-operative disease progression metrics for individual reference patients, (ii) disease metrics at the time of surgical intervention for individual reference patients, (iii) post-operative disease progression metrics for individual reference patients, and/or (iv) scored surgical outcomes for individual reference patients. The intervention timing module can compare the disease metrics for a particular patient to the reference patient data sets to determine, for similar patients, the point of disease progression at which surgical intervention produced the most favorable outcomes.

As a non-limiting example, the reference patient data sets may include data associated with reference patients' sagittal vertical axis. The data can include (i) sagittal vertical axis values for individual patients over a period of time before surgical intervention (e.g., how fast and to what degree the sagittal vertical axis value changed), (ii) sagittal vertical axis of the individual patients at the time of surgical intervention, (iii) the change in sagittal vertical axis after surgical intervention, and (iv) the degree to which the surgical intervention was successful (e.g., based on pain, quality of life, or other factors). Based on the foregoing data, the intervention timing module can, based on a particular patient's sagittal vertical axis value, identify at which point surgical intervention will have the highest likelihood of producing the most favorable outcome. Of course, the foregoing metric is provided by way of example only, and the intervention timing module can incorporate other metrics (e.g., lumbar lordosis, pelvic tilt, sagittal vertical axis, cobb angel, coronal offset, disability scores, functional ability scores, flexibility scores, VAS pain scores, sacroiliac joint stability, sacroiliac joint flexibility, sacroiliac joint range of motion, sacroiliac joint loading, simulated sacroiliac joint loading, etc.) instead of or in combination with sagittal vertical axis to predict the time at which surgical intervention has the highest probability of providing a favorable outcome for the particular patient.

The intervention timing module may also incorporate one or more mathematical rules based on value thresholds for various disease metrics. For example, the intervention timing module may indicate surgical intervention is necessary if one or more disease metrics exceed a predetermined threshold or meet some other criteria. Representative thresholds that indicate surgical intervention may be necessary include SVA values greater than 7 mm, a mismatch between lumbar lordosis and pelvic incidence greater than 10 degrees, a cobb angle of greater than 10 degrees, and/or a combination of cobb angle and LL/PI mismatch greater than 20 degrees. Of course, other threshold values and metrics can be used; the foregoing are provided as examples only and in no way limit the present disclosure. In some embodiments, the foregoing rules can be tailored to specific patient populations (e.g., for males over 50 years of age, an SVA value greater than 7 mm indicates the need for surgical intervention). If a particular patient does not exceed the thresholds indicating surgical intervention is recommended, the intervention timing module may provide an estimate for when the patient's metrics will exceed one or more thresholds, thereby providing the patient with an estimate of when surgical intervention may become recommended.

The present technology may also include a treatment planning module that can identify the optimal type of surgical procedure for the patient based on the disease progression of the patient. The treatment planning module can be an algorithm, machine learning model, or other software analytical tool trained or otherwise based on a plurality of reference patient data sets, as previously described. The treatment planning module may also incorporate one or more mathematical rules for identifying surgical procedures. As a non-limiting example, if a LL/PI mismatch is between 10 and 20 degrees, the treatment planning module may recommend an anterior fusion surgery, but if the LL/PI mismatch is greater than 20 degrees, the treatment planning module may recommend both anterior and posterior fusion surgery. As another non-limiting example, if a SVA value is between 7 mm and 15 mm, the treatment planning module may recommend posterior fusion surgery, but if the SVA is above 15 mm, the treatment planning module may recommend both posterior fusion surgery and anterior fusion surgery. Of course, other rules can be used; the foregoing are provided as examples only and in no way limit the present disclosure.

Without being bound by theory, incorporating disease progression modeling into the patient-specific medical procedures described herein may even further increase the effectiveness of the procedures. For example, in many cases it may be disadvantageous to operate after a patient's disease progresses to an irreversible or unstable state. However, it may also be disadvantageous to operate too early, e.g., before the patient's disease is causing symptoms and/or if the patient's disease may not progress further. The disease progression module and/or the intervention timing module can therefore help identify the window of time during which surgical intervention in a particular patient has the highest probability of providing a favorable outcome for the patient.

As one skilled in the art will appreciate, any of the software modules described previously may be combined into a single software module for performing the operations described herein. Likewise, the software modules can be distributed across any combination of the computing systems and devices described herein, and are not limited to the express arrangements described herein. Accordingly, any of the operations described herein can be performed by any of the computing devices or systems described herein, unless expressly noted otherwise.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In some embodiments, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable-type medium such as a floppy disk, a hard disk drive, a CD, a DVD, a digital tape, a computer memory, etc.; and a transmission type medium such as a digital and/or an analog communication medium (e.g., a fiber optic cable, a waveguide, a wired communications link, a wireless communication link, etc.).

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely examples, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermediate components. Likewise, any two components so associated can also be viewed as being "operably connected," or "operably coupled," to each other to achieve the desired functionality, and any two components capable of being so associated can also be viewed as being "operably couplable" to each other to achieve the desired functionality. Specific examples of operably couplable include but are not limited to physically mateable and/or physically interacting components and/or wirelessly interactable and/or wirelessly interacting components and/or logically interacting and/or logically interactable components.

The embodiments, features, systems, devices, materials, methods and techniques described herein may, in some embodiments, be similar to any one or more of the embodiments, features, systems, devices, materials, methods and techniques described in the following

- U.S. application Ser. No. 16/048,167, filed on Jul. 27, 2017, titled "SYSTEMS AND METHODS FOR ASSISTING AND AUGMENTING SURGICAL PROCEDURES;"
- U.S. application Ser. No. 16/242,877, filed on Jan. 8, 2019, titled "SYSTEMS AND METHODS OF ASSISTING A SURGEON WITH SCREW PLACEMENT DURING SPINAL SURGERY;"
- U.S. application Ser. No. 16/207,116, filed on Dec. 1, 2018, titled "SYSTEMS AND METHODS FOR MULTI-PLANAR ORTHOPEDIC ALIGNMENT;"
- U.S. application Ser. No. 16/352,699, filed on Mar. 13, 2019, titled "SYSTEMS AND METHODS FOR ORTHOPEDIC IMPLANT FIXATION;"
- U.S. application Ser. No. 16/383,215, filed on Apr. 12, 2019, titled "SYSTEMS AND METHODS FOR ORTHOPEDIC IMPLANT FIXATION;"
- U.S. application Ser. No. 16/569,494, filed on Sep. 12, 2019, titled "SYSTEMS AND METHODS FOR ORTHOPEDIC IMPLANTS;"
- U.S. application Ser. No. 16/669,447, filed on Nov. 29, 2019, titled "SYSTEMS AND METHODS FOR ORTHOPEDIC IMPLANTS;"
- U.S. application Ser. No. 17/085,564, filed on Oct. 30, 2020, titled "SYSTEMS AND METHODS FOR DESIGNING ORTHOPEDIC IMPLANTS BASED ON TISSUE CHARACTERISTICS;"
- U.S. application Ser. No. 16/735,222, filed Jan. 6, 2020, titled "PATIENT-SPECIFIC MEDICAL PROCEDURES AND DEVICES, AND ASSOCIATED SYSTEMS AND METHODS;"
- U.S. application Ser. No. 16/987,113, filed Aug. 6, 2020, titled "PATIENT-SPECIFIC ARTIFICIAL DISCS, IMPLANTS AND ASSOCIATED SYSTEMS AND METHODS;"
- U.S. application Ser. No. 16/990,810, filed Aug. 11, 2020, titled "LINKING PATIENT-SPECIFIC MEDICAL DEVICES WITH PATIENT-SPECIFIC DATA, AND ASSOCIATED SYSTEMS, DEVICES, AND METHODS;"
- U.S. application Ser. No. 17/100,396, filed Nov. 20, 2020, titled "PATIENT-SPECIFIC VERTEBRAL IMPLANTS WITH POSITIONING FEATURES;"
- U.S. Application No. 63/116,436, filed Nov. 20, 2020, titled "PATIENT-SPECIFIC JIG FOR PERSONALIZED SURGERY;"
- U.S. application Ser. No. 17/124,822, filed Dec. 17, 2020, titled "PATIENT-SPECIFIC MEDICAL PROCEDURES AND DEVICES, AND ASSOCIATED SYSTEMS AND METHODS;"
- U.S. application Ser. No. 17/342,439, filed Jun. 8, 2021, titled "PATIENT-SPECIFIC MEDICAL SYSTEMS, DEVICES, AND METHODS;"
- U.S. application Ser. No. 17/463,054, filed Aug. 31, 2021, titled "BLOCKCHAIN MANAGED MEDICAL IMPLANTS;"
- U.S. application Ser. No. 17/835,777, filed Jun. 8, 2022, titled "PATIENT-SPECIFIC EXPANDABLE SPINAL IMPLANTS AND ASSOCIATED SYSTEMS AND METHODS;"
- U.S. application Ser. No. 17/842,242, filed Jun. 16, 2022, titled "PATIENT-SPECIFIC ANTERIOR PLATE IMPLANTS;" and
- U.S. application Ser. No. 17/851,487, filed Jun. 28, 2022, titled "PATIENT-SPECIFIC ADJUSTMENT OF SPINAL IMPLANTS, AND ASSOCIATED SYSTEMS AND METHODS."

All of the above-identified patents and applications are incorporated by reference in their entireties. In addition, the embodiments, features, systems, devices, materials, methods and techniques described herein may, in certain embodiments, be applied to or used in connection with any one or more of the embodiments, features, systems, devices, or other matter.

The ranges disclosed herein also encompass any and all overlap, sub-ranges, and combinations thereof. Language such as "up to," "at least," "greater than," "less than," "between," or the like includes the number recited. Numbers preceded by a term such as "approximately," "about," and "substantially" as used herein include the recited numbers (e.g., about 10%=10%), and also represent an amount close to the stated amount that still performs a desired function or achieves a desired result. For example, the terms "approximately," "about," and "substantially" may refer to an amount that is within less than 10% of, within less than 5% of, within less than 1% of, within less than 0.1% of, and within less than 0.01% of the stated amount.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting.

What is claimed is:

1. A computer-implemented method for designing one or more patient-specific sacroiliac implants for addressing sacroiliac dysfunction, the method comprising:

receiving patient data, the patient data including— image data of a pelvic region of a patient, including at least portions of a sacrum, an ilium, and a sacroiliac joint of the patient, and scores associated with dysfunction at the patient's pelvic region;

generating a virtual three-dimensional model of the patient's pelvic region based on the image data, the virtual three-dimensional model including at least portions of the sacrum, the ilium, and the sacroiliac joint of the patient;

analyzing the virtual three-dimensional model and the scores to determine one or more anatomical features of portions of the sacrum and the ilium that at least partially define the sacroiliac joint, and one or more surgical corrections to the patient's pelvic region, wherein the one or more surgical corrections include (1) a corrective adjustment to a relative positioning of the patient's sacrum and the ilium, and (2) fusion of the patient's sacroiliac joint to maintain the corrective adjustment;

designing the one or more patient-specific sacroiliac implants sized and shaped to be positioned at least partially within the patient's sacroiliac joint to provide the corrective adjustment and to fuse the sacroiliac joint to maintain the corrective adjustment based at least in part on the one or more anatomical features, including determining a post-operative sagittal vertical axis and a post-operative Cobb angle, wherein the post-operative sagittal vertical axis is less than 7 millimeters, and the post-operative Cobb angle is less than 10 degrees, and wherein the one or more patient-specific sacroiliac implants include:

a first patient-specific surface contoured to match a surface of the sacrum that defines a portion of the patient's sacroiliac joint, and a second patient-specific surface contoured to match a surface of the ilium that defines a portion of the patient's sacroiliac joint; and determining one or more sacroiliac joint-related surgical steps for implanting the one or more patient-specific sacroiliac implants within the patient's sacroiliac joint.

2. The computer-implemented method of claim 1 wherein the one or more patient-specific sacroiliac implants includes a plurality of patient-specific sacroiliac fusion devices.

3. The computer-implemented method of claim 1, further comprising:

predicting a post-operative shear force that will be applied to the one or more patient-specific sacroiliac implants once the one or more patient-specific sacroiliac implants are implanted in the patient; and designing the one or more patient-specific sacroiliac implants to withstand a shear force that is at least 50% greater than the predicted post-operative shear force.

4. The computer-implemented method of claim 3 wherein predicting the post-operative shear force includes predicting a first post-operative shear force when the patient is standing and a second post-operative shear force when the patient is sitting, and wherein the one or more patient-specific sacroiliac implants are designed to withstand a shear force that is at least 50% greater than whichever of the first post-operative shear force or the second post-operative shear force is greater.

5. The computer-implemented method of claim 1, further comprising:

before determining the one or more surgical corrections to the patient's pelvic region, analyzing the virtual model and the scores to confirm pain of the patient is caused by dysfunction at the sacroiliac joint and is a candidate for corrective surgery.

6. The computer-implemented method of claim 5 wherein analyzing the virtual model and the scores includes using a trained machine learning model, wherein the machine learning model was trained based on previous patient virtual models, pain scores, and surgical outcomes.

7. The computer-implemented method of claim 1 wherein the one or more anatomical features of the portions of the sacrum and the ilium include surface topographies of the portions of the sacrum and the ilium.

8. The computer-implemented method of claim 1 wherein the first patient-specific surface and the second patient-specific surface create a continuous interface between the surface of the sacrum and the surface of the ilium, respectively.

9. The computer-implemented method of claim 1 wherein designing the one or more patient-specific sacroiliac implants includes determining a density of the one or more patient-specific sacroiliac implants based at least in part on the one or more anatomical features of the sacroiliac joint.

10. The computer-implemented method of claim 1 wherein designing the one or more patient-specific sacroiliac implants includes selecting a material of the one or more patient-specific sacroiliac implants based at least in part on the one or more anatomical features of the sacroiliac joint.

11. A computer-implemented method for designing at least one patient-specific sacroiliac joint implant, the method comprising:

generating a virtual three-dimensional model of at least a portion of a spinal anatomy of a patient, including at least a portion of a sacroiliac joint, a sacrum, and an ilium of the patient;

determining a corrected configuration for at least the portion of the patient's spinal anatomy;

analyzing the virtual three-dimensional model to determine (i) anatomical features of portions of the ilium and the sacrum that at least partially define the sacroiliac joint and (ii) a target position of the ilium and the sacrum for repositioning the patient's spinal anatomy in the corrected configuration; and designing the at least one patient-specific sacroiliac joint implant sized and shaped to be positioned at least partially within the patient's sacroiliac joint and coupled to the ilium and the sacrum to maintain the ilium and the sacrum in the target position based at least in part on the anatomical features, including determining a post-operative sagittal vertical axis and a post-operative Cobb angle, wherein the post-operative sagittal vertical axis is less than 7 millimeters, and the post-operative Cobb angle is less than 10 degrees, and wherein the at least one patient-specific sacroiliac joint implant includes:

a first patient-specific surface contoured to match a surface of the sacrum that defines a portion of the patient's sacroiliac joint, and a second patient-specific surface contoured to match a surface of the ilium that defines a portion of the patient's sacroiliac joint.

12. The computer-implemented method of claim 11, wherein analyzing the virtual three-dimensional model includes:

moving the virtual three-dimensional model of the patient's spinal anatomy to the corrected configuration;

determining the target position of the ilium and the sacrum based at least partially on the movement of the virtual three-dimensional model to the corrected configuration; and identifying an implant location along the patient's sacroiliac joint based on the determined target position.

13. The computer-implemented method of claim 11, further comprising:

simulating loading on the sacroiliac joint for a range of motion of a spine of the patient;

determining acceptable loading for the sacroiliac joint of the patient based at least partially on the simulated loading; and comparing the acceptable loading with the simulated loading to determine whether the simulated loading is within an acceptable loading threshold.

14. The computer-implemented method of claim 11, further comprising:

receiving patient pain data;

determining one or more adjustments to the virtual three-dimensional model of the patient's spinal anatomy based at least partially on the received patient pain data; and determining a pain reduction score based on the one or more spinal adjustments prior to manufacturing the at least one patient-specific sacroiliac joint implant.

15. The computer-implemented method of claim 11, further comprising performing, using the virtual three-dimensional model, a biomechanical simulation of spinal load transfer via the sacroiliac joint to a coxal bone of the patient.

16. The computer-implemented method of claim 11, further comprising performing a biomechanical simulation of spinal load transfer via the sacroiliac joint to a coxal bone of the patient.

17. The computer-implemented method of claim 11, wherein analyzing the virtual three-dimensional model includes predicting a post-operative compressive force and/or a post-operative shear force in the sacroiliac joint.

18. The computer-implemented method of claim 17, wherein designing the at least one patient-specific sacroiliac joint implant includes designing the sacroiliac joint to withstand a compressive force and/or a shear force that is at least 50% greater than the predicted post-operative compressive force and/or the predicted post-operative shear force.

19. The computer-implemented method of claim 11, wherein analyzing the virtual three-dimensional model includes:

modeling one or more muscles and/or ligaments associated with the patient's spinal anatomy; and predicting forces applied to the sacroiliac joint based on (i) the modeling of the one or more muscles and the ligaments, and (ii) a simulated loading on a spine of the patient.

20. The computer-implemented method of claim 11, further comprising:

simulating one or more sacroiliac joint adjustments; and performing one or more pre-operative and/or post-operative simulations to predict a patient outcome based on the one or more simulated sacroiliac joint adjustments.

21. The computer-implemented method of claim 11, wherein the at least one patient-specific sacroiliac joint implant has a first topology configured to match a second topology of the patient's sacroiliac joint at or near the target position.

22. The computer-implemented method of claim 11, wherein the at least one patient-specific sacroiliac joint implant has a first topology configured to match a second topology of a coxal bone of the patient.

23. The computer-implemented method of claim 11, further comprising:

identifying one or more regions of a spine of the patient for adjustment; and adjusting one or more anatomic elements of the virtual three-dimensional model at the identified one or more regions to produce the corrected configuration for the patient's spine.

24. The computer-implemented method of claim 11 wherein the anatomical features of the portions of the ilium and the sacrum include surface topographies of the portions of the sacrum and the ilium, and wherein the surface topographies are different.

25. A method of manufacturing a patient-specific sacroiliac fusion device for addressing sacroiliac dysfunction in a patient, the method comprising:

receiving manufacturing data for the patient-specific sacroiliac fusion device, wherein the patient-specific sacroiliac fusion device is configured to (1) provide a corrective adjustment to a relative position of a sacrum and/or an ilium of the patient when implanted in the patient, and (2) fuse a sacroiliac joint of the patient to maintain the corrective adjustment, and wherein the manufacturing data is generated by a process including:

generating a virtual three-dimensional model of a pelvic region of the patient, including at least a portion of the sacrum, the ilium, and the sacroiliac joint, and based at least in part on the virtual three-dimensional model, determining (1) anatomical features of the sacrum and the ilium that at least partially define the sacroiliac joint and (2) the corrective adjustment to the relative position of the sacrum and the ilium;

designing the patient-specific sacroiliac fusion device to provide and maintain the corrective adjustment based at least in part on the anatomical features, including determining a post-operative sagittal vertical axis and a post-operative Cobb angle, wherein the post-operative sagittal vertical axis is less than 7 millimeters, and the post-operative Cobb angle is less than 10 degrees, and wherein the patient-specific sacroiliac fusion device is sized and shaped to be positioned at least partially within the patient's sacroiliac joint and includes:

a first patient-specific surface contoured to match a surface of the sacrum that defines a portion of the patient's sacroiliac joint, and a second patient-specific surface contoured to match a surface of the ilium that defines a portion of the patient's sacroiliac joint;

converting the manufacturing data into computer-executable instructions; and using the computer-executable instructions to manufacture the patient-specific sacroiliac fusion device.

26. The method of claim 25 wherein the anatomical features of the portions of the ilium and the sacrum include surface topographies of the portions of the sacrum and the ilium, and wherein the surface topographies are different.

27. A computer-implemented method for designing one or more patient-specific sacroiliac implants for addressing sacroiliac dysfunction, the method comprising:

receiving patient data, the patient data including— image data of a pelvic region of a patient, including at least portions of a sacrum, an ilium, and a sacroiliac joint of the patient, and scores associated with dysfunction at the patient's pelvic region;

generating a virtual three-dimensional model of the patient's pelvic region based on the image data, the virtual three-dimensional model including at least portions of the sacrum, the ilium, and the sacroiliac joint of the patient;

analyzing the virtual three-dimensional model and the scores to determine one or more anatomical features of portions of the sacrum and the ilium that at least partially define the sacroiliac joint, and one or more surgical corrections to the patient's pelvic region, wherein the one or more surgical corrections include (1) a corrective adjustment to a relative positioning of the patient's sacrum and the ilium, and (2) fusion of the patient's sacroiliac joint to maintain the corrective adjustment;

designing the one or more patient-specific sacroiliac implants sized and shaped to be positioned at least partially within the patient's sacroiliac joint to provide the corrective adjustment and to fuse the sacroiliac joint to maintain the corrective adjustment based at least in part on the one or more anatomical features, wherein the one or more patient-specific sacroiliac implants are designed to withstand compressive and shear forces at least 200% greater than predicted post-operative compressive and shear forces, and wherein the one or more patient-specific sacroiliac implants include:

a first patient-specific surface contoured to match a surface of the sacrum that defines a portion of the patient's sacroiliac joint, and a second patient-specific surface contoured to match a surface of the ilium that defines a portion of the patient's sacroiliac joint; and determining one or more sacroiliac joint-related surgical steps for implanting the one or more patient-specific sacroiliac implants within the patient's sacroiliac joint.

28. A computer-implemented method for designing one or more patient-specific sacroiliac implants for addressing sacroiliac dysfunction, the method comprising:

receiving patient data, the patient data including— image data of a pelvic region of a patient, including at least portions of a sacrum, an ilium, and a sacroiliac joint of the patient, and scores associated with dysfunction at the patient's pelvic region;

generating a virtual three-dimensional model of the patient's pelvic region based on the image data, the virtual three-dimensional model including at least portions of the sacrum, the ilium, and the sacroiliac joint of the patient;

analyzing the virtual three-dimensional model and the scores to determine one or more anatomical features of portions of the sacrum and the ilium that at least partially define the sacroiliac joint, and one or more surgical corrections to the patient's pelvic region, wherein the one or more surgical corrections include (1) a corrective adjustment to a relative positioning of the patient's sacrum and the ilium, and (2) fusion of the patient's sacroiliac joint to maintain the corrective adjustment;

designing a first patient-specific sacroiliac implant sized and shaped to be positioned internally to the patient's sacroiliac joint and coupled to interior surfaces of the ilium and the sacrum, wherein the first patient-specific sacroiliac implant includes:

a first patient-specific surface contoured to match the surface of the sacrum that defines the portion of the patient's sacroiliac joint, and a second patient-specific surface contoured to match the surface of the ilium that defines the portion of the patient's sacroiliac joint;

designing a second patient-specific sacroiliac implant sized and shaped to be positioned externally to the patient's sacroiliac joint and coupled to external surfaces of the ilium and the sacrum; and determining one or more sacroiliac joint-related surgical steps for implanting the one or more patient-specific sacroiliac implants.

* * * * *